US011026762B2

(12) United States Patent
Kuramoto

(10) Patent No.: US 11,026,762 B2
(45) Date of Patent: Jun. 8, 2021

(54) MEDICAL OBSERVATION DEVICE, PROCESSING METHOD, AND MEDICAL OBSERVATION SYSTEM

(71) Applicant: Sony Olympus Medical Solutions Inc., Tokyo (JP)

(72) Inventor: Seiji Kuramoto, Kanagawa (JP)

(73) Assignee: SONY OLYMPUS MEDICAL SOLUTIONS INC., Tokyo (JP)

(*) Notice: Subject to any disclaimer, the term of this patent is extended or adjusted under 35 U.S.C. 154(b) by 0 days.

(21) Appl. No.: 16/614,801

(22) PCT Filed: Mar. 2, 2018

(86) PCT No.: PCT/JP2018/008074
§ 371 (c)(1),
(2) Date: Nov. 19, 2019

(87) PCT Pub. No.: WO2018/216302
PCT Pub. Date: Nov. 29, 2018

(65) Prior Publication Data
US 2020/0197122 A1 Jun. 25, 2020

(30) Foreign Application Priority Data
May 26, 2017 (JP) .............................. JP2017-104928

(51) Int. Cl.
*A61B 90/20* (2016.01)
*H04N 5/232* (2006.01)
(Continued)

(52) U.S. Cl.
CPC .............. *A61B 90/20* (2016.02); *A61B 34/74* (2016.02); *G06F 3/167* (2013.01); *H04N 5/23203* (2013.01)

(58) Field of Classification Search
CPC .................................................. G02B 21/365
(Continued)

(56) References Cited

U.S. PATENT DOCUMENTS

| 3,887,267 | A |   | 6/1975 | Heller |             |
|-----------|---|---|--------|--------|-------------|
| 4,034,743 | A | * | 7/1977 | Greenwood | A61B 5/08 |
|           |   |   |        |        | 600/538     |

(Continued)

FOREIGN PATENT DOCUMENTS

| EP | 2 116 209 A1 | 11/2009 |
| EP | 3 144 711 A1 | 3/2017 |

(Continued)

OTHER PUBLICATIONS

International Search Report and Written Opinion dated May 15, 2018 for PCT/JP2018/008074 filed on Mar. 2, 2018, 14 pages including English Translation of the International Search Report.

(Continued)

*Primary Examiner* — Paulos M Natnael
(74) *Attorney, Agent, or Firm* — Xsensus LLP

(57) ABSTRACT

Provided is a medical observation device which includes a detection unit configured to detect a pressing operation based on an operation signal according to the pressing operation which is output from an external operation device equipped with a switch pressed by a mouth, and a processing unit configured to perform a process corresponding to the detected pressing operation. The process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

19 Claims, 11 Drawing Sheets

(51) Int. Cl.
*A61B 34/00* (2016.01)
*G06F 3/16* (2006.01)

(58) Field of Classification Search
USPC ...................................................... 348/79–80
See application file for complete search history.

(56) References Cited

U.S. PATENT DOCUMENTS

| | | | |
|---|---|---|---|
| 4,989,253 A | | 1/1991 | Liang et al. |
| 5,040,975 A | * | 8/1991 | Ettwein .................... A61C 7/02 |
| | | | 433/27 |
| 5,867,308 A | | 2/1999 | Pensel et al. |
| 8,309,837 B2 | * | 11/2012 | Hashimoto ............ G10H 1/053 |
| | | | 84/737 |
| 8,454,527 B2 | * | 6/2013 | Aljuri ............... A61M 16/0404 |
| | | | 600/532 |
| 8,523,782 B2 | * | 9/2013 | Freitag ................. A61B 5/6852 |
| | | | 600/538 |
| 9,557,331 B2 | * | 1/2017 | Bangera ................. A61B 10/02 |
| 2007/0206274 A1 | | 9/2007 | Nakamura |
| 2009/0185034 A1 | * | 7/2009 | Kishida ................ G02B 21/365 |
| | | | 348/79 |
| 2011/0013010 A1 | * | 1/2011 | Shirota ................. G06F 3/0488 |
| | | | 348/79 |
| 2015/0224643 A1 | | 8/2015 | Ernsperger et al. |
| 2017/0143442 A1 | | 5/2017 | Tesar et al. |

FOREIGN PATENT DOCUMENTS

| | | |
|---|---|---|
| JP | 50-37448 A | 4/1975 |
| JP | 62-166312 A | 7/1987 |
| JP | 4-324409 A | 11/1992 |
| JP | 3092943 B2 | 9/2000 |
| JP | 2005-87528 A | 4/2005 |
| JP | 2014-523537 A | 9/2014 |
| JP | 2015-150436 A | 8/2015 |
| WO | 2005/099609 A1 | 10/2005 |
| WO | 2012/130449 A1 | 10/2012 |

OTHER PUBLICATIONS

Extended European Search Report dated Jul. 20, 2020 in European Patent Application No. 18806183.2, 19 pages.

* cited by examiner

FIG.4
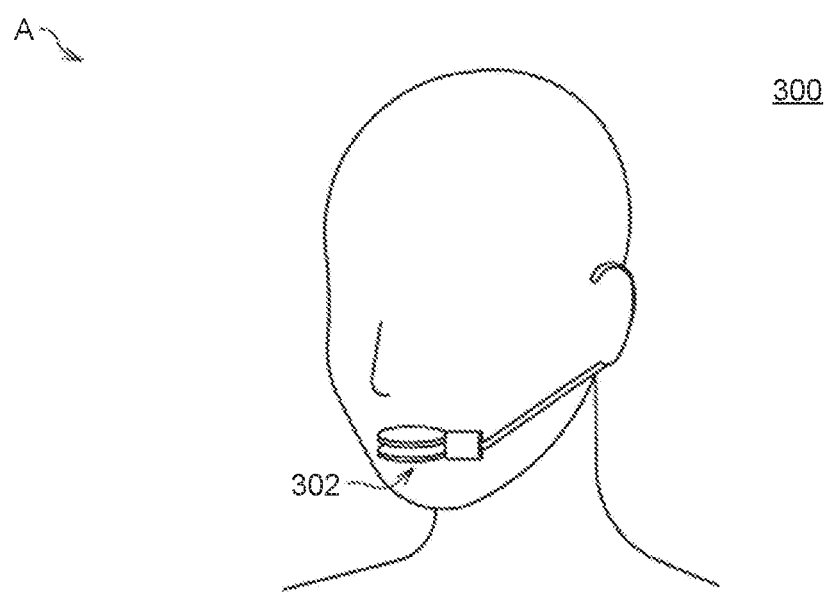
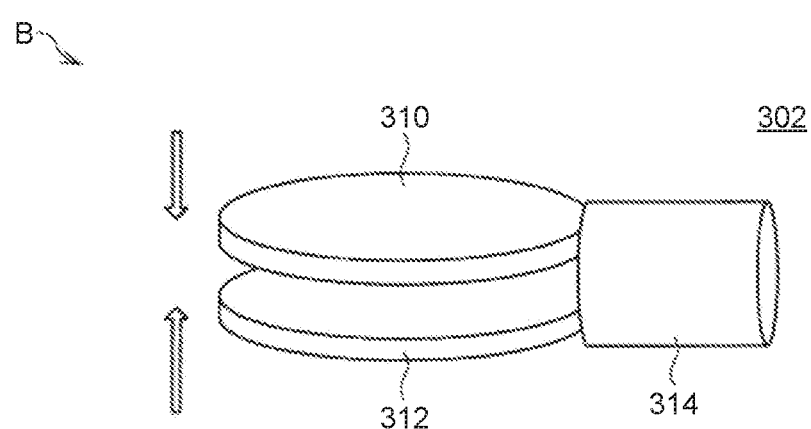

MEDICAL OBSERVATION DEVICE, PROCESSING METHOD, AND MEDICAL OBSERVATION SYSTEM

CROSS-REFERENCE TO RELATED APPLICATIONS

The present application is based on PCT filing PCT/JP2018/008074, filed Mar. 2, 2018, which claims priority to JP 2017-104928, filed May 26, 2017, the entire contents of each are incorporated herein by reference.

TECHNICAL FIELD

The present disclosure relates to a medical observation device, a processing method, and a medical observation system.

BACKGROUND ART

In recent years, in medical fields, a medical observation device capable of magnifying and observing an observation target such as an affected part may be used to support microsurgeries such as brain nerve surgery. Examples of the medical observation device include a medical observation device which includes an optical microscope, and a medical observation device which includes an imaging device serving as an electronic microscope. In the following, the medical observation device equipped with the optical microscope is referred to as "an optical medical observation device". In addition, in the following, the medical observation device equipped with the imaging device may be referred to as "the electronic medical observation device" or simply "the medical observation device".

In addition, a technology for simplifying a moving operation in the optical medical observation device is developed. As a technology for simplifying the moving operation in the optical medical observation device using the pressing operation unit which is pressed by a mouth, the technique of Patent Literature 1 below is disclosed.

CITATION LIST

Patent Literature

Patent Literature 1: JP 2005-87528 A

DISCLOSURE OF INVENTION

Technical Problem

The electronic medical observation device obtains an image quality equal to or higher than that of the optical medical observation device in accordance with high image quality of the imaging device and high image quality of a display device displaying the captured image. In addition, the user (for example, a medical worker such as an operator or an assistant of the operator) who uses the electronic medical observation device does not necessarily look in an eyepiece of the optical microscope unlike the optical medical observation device. Therefore, the position of the imaging device can be moved more freely. Therefore, the use of the electronic medical observation device has an advantage that the use of the electronic medical observation device can more flexibly support the fine operation, and the use of the electronic medical observation device at a medical site is advanced.

For example, when a surgical operation is performed using the electronic medical observation device, the operator may need to change an imaging operation of the imaging device of the electronic medical observation device. In order to respond to the operator's request, there is a need of an operation device such as a switch which is capable of changing the imaging operation of the imaging device in the electronic medical observation device. In addition, the electronic medical observation device is configured to operate without releasing the operator's both hands from an operating field using an external foot switch of the electronic medical observation device.

In order to perform the operation of the electronic medical observation device without releasing both hands from the operating field during a surgical operation, the operator uses the foot switch. However, in an operating room, there may be lots of foot switches to operate various medical treatment devices such as an electric scalpel and an ultrasonic suction device in addition to the foot switch for the operation of the electronic medical observation device. Therefore, there is required a user interface instead of the foot switch in order to prevent an erroneous operation of the devices in the medical sites.

Herein, for example as the user interface instead of the foot switch, there is a switch (hereinbelow, this may be referred to as "mouth switch") which is pressed by a mouth as disclosed in Patent Literature 1. The operator who uses the optical medical observation device according to the technique disclosed in Patent Literature 1 looks in the eyepiece of the optical microscope, so that the mouth switch can be operated in a state of looking in the eyepiece.

However, the medical observation device of the electronic imaging type is not configured to include the eyepiece unlike the optical medical observation device, and the imaging device can freely move. Thus, the position of an operator's face and the position of the imaging device are not constant. Therefore, even though the mouth switch is installed in the electronic medical observation device, it cannot be said that the operator can always operate the medical observation device using the mouse switch without releasing both hands in the operating field.

An object of the present disclosure is to provide a medical observation device, a processing method, and a medical observation system which is new and improved, and can operate the medical observation device using an external operation device equipped with the switch which is pressed by a mouth.

Solution to Problem

According to the present disclosure, there is provided a medical observation device, including: a detection unit configured to detect a pressing operation based on an operation signal according to the pressing operation output from an external operation device equipped with a switch pressed by a mouth; and a processing unit configured to perform a process corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

Moreover, according to the present disclosure, there is provided a processing method performed by a medical observation device, the method including the steps of: detecting a pressing operation based on an operation signal according to the pressing operation output from an external operation device equipped with a switch pressed by a mouth; and performing a process corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

Moreover, according to the present disclosure, there is provided a medical observation system, including: an operation device including a switch pressed by a mouth; and a medical observation device, wherein the medical observation device includes an imaging device, a detection unit configured to detect the pressing operation based on an operation signal according to the pressing operation output from the operation device, and a processing unit configured to perform a process corresponding to the detected pressing operation, and wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

Advantageous Effects of Invention

According to the present disclosure, the medical observation device can be operated by an external operation device equipped with a switch which is pressed by a mouth.

Further, the disclosure is not necessarily limited to the above effect, but any of the effects shown in this specification or other effects that may be grasped from this specification may be achieved together with or in place of the above effect.

BRIEF DESCRIPTION OF DRAWINGS

FIG. 4 is an explanatory diagram for describing an example of an operation device according to this embodiment.

BEST MODE FOR CARRYING OUT THE INVENTION

Hereinbelow, preferred embodiments of the present disclosure will be described in detail with reference to the accompanying drawings. Further, the components having substantially the same functional configuration in the specification and the drawings will be attached with the same symbol, and the redundant description will be omitted.

In addition, the description below will be given in an order as follows.

1. A medical observation system according to this embodiment, and a processing method according to this embodiment 2. A program according to this embodiment (Medical Observation System According to Embodiment, and Processing Method According to Embodiment)

Hereinbelow, the processing method according to this embodiment will be described with an example of the medical observation system according to this embodiment.

[1] Configuration of Medical Observation System

Figure 1:
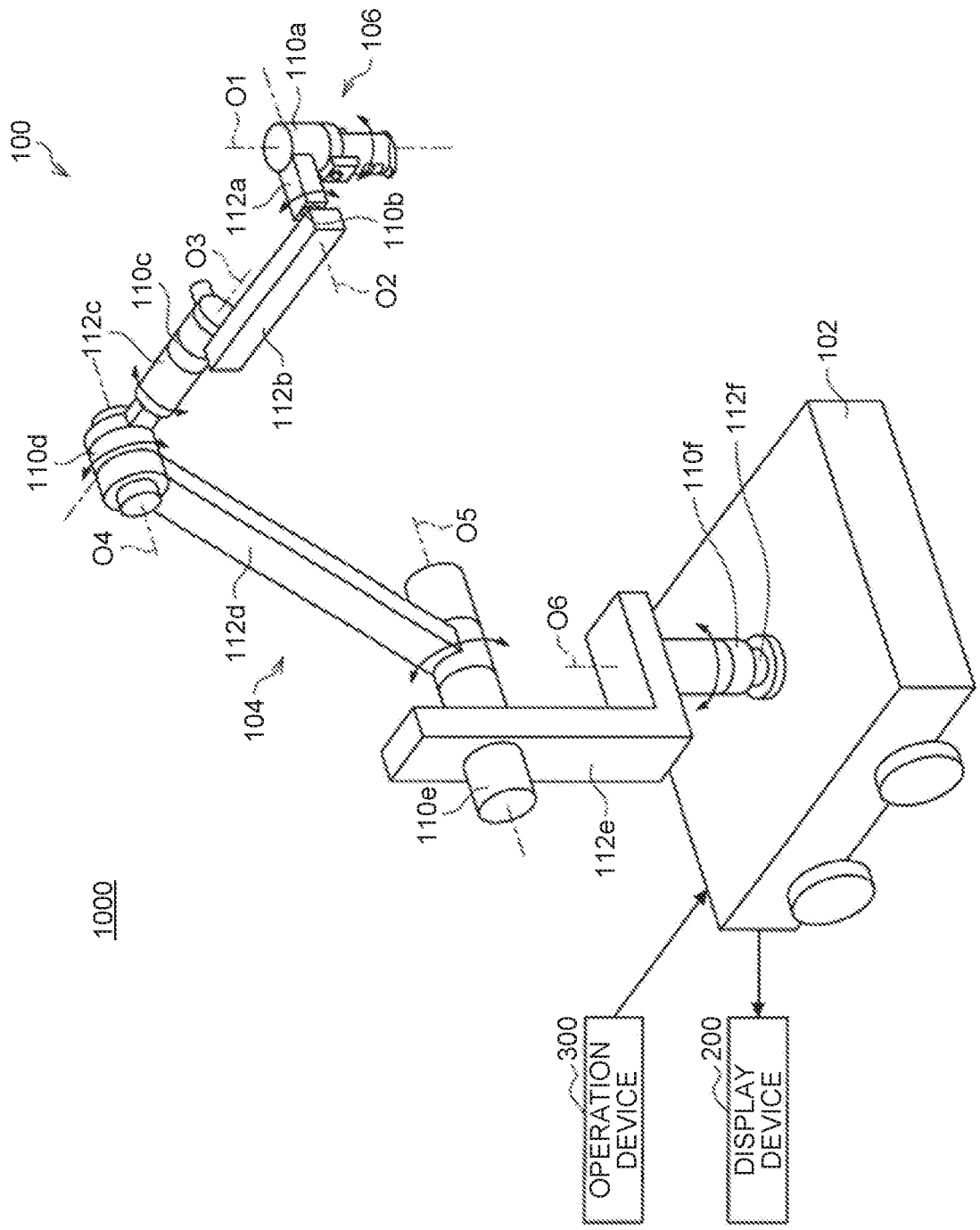
FIG. 1 is an explanatory diagram illustrating an example of a configuration of a medical observation system according to an embodiment.

FIG. 1 is an explanatory diagram illustrating an example of a configuration of a medical observation system 1000 according to an embodiment. The medical observation system 1000 includes, for example, a medical observation device 100, a display device 200, and an operation device 300.

Further, the medical observation system according to this embodiment is not limited to the example illustrated in FIG. 1.

For example, the medical observation system according to this embodiment may also include a control device (not illustrated) which controls various types of operations in the medical observation device 100. In the medical observation system 1000 illustrated in FIG. 1, as described below, the medical observation device 100 includes a control unit (described below) which performs a process related to the processing method according to this embodiment. Therefore, the medical observation device 100 has a function of the control device (not illustrated).

The control device (not illustrated) includes, for example, any device capable of performing a process related to the processing method according to this embodiment such as "medical controller" and "computer such as a server". In addition, the control device (not illustrated) may be an IC (Integrated Circuit) which can be combined to the above device.

In addition, the medical observation system according to this embodiment may be configured to include a plurality of medical observation devices 100 and a plurality of display devices 200. In a case where there are provided the medical observation devices 100, each of the medical observation devices 100 performs a process related to the processing method in the medical observation device 100 described below. In addition, in a case where the medical observation system according to this embodiment is configured to include the medical observation devices 100 and the display devices 200, the medical observation devices 100 and the display devices 200 may be associated to each other in a one-to-one manner, or the medical observation devices 100 may be associated to one display device 200. In a case where the medical observation devices 100 is associated to one display device 200, the display device 200 performs, for example, a switching operation to switch images captured in the medical observation devices 100 to be displayed in a display screen.

In addition, the medical observation system according to this embodiment may be configured to include a plurality of operation devices 300. In a case where there are provided the operation devices 300, the medical observation device 100 can operate based on the operation on each of the operation devices 300. In addition, in a case where there are provided the operation devices 300, the medical observation device 100 may operate based on the operation on some operation devices 300 (the operation device 300 with a highest priority setting among the operation devices 300, and the operation devices 300 having a priority equal to or more than a threshold setting) among the operation devices 300.

In addition, the medical observation system according to this embodiment may include one or two or more sensors such as a line-of-vision detecting sensor capable of detecting a line of vision, and a motion detecting sensor capable of detecting a motion. The line-of-vision detecting sensor and the motion detecting sensor may be the same sensor, or different sensors. A sensor serving as the line-of-vision detecting sensor and the motion detecting sensor includes "a sensor unit which includes a stereo camera and a processor, and detects one or both of the line of vision and the motion from an image captured by the stereo camera". In addition, in a case where the line-of-vision detecting sensor and the motion detecting sensor are different sensors, the line-of-vision detecting sensor may be any type of sensors which can detects the line of vision such as a configuration of detecting the line of vision using an infrared ray. In addition, in a case where the line-of-vision detecting sensor and the motion detecting sensor are different sensors, the motion detecting sensor may be any type of sensors which can detect a motion such as a configuration of detecting a motion using a ToF (Time-of-Flight) manner.

In a case where the medical observation system according to this embodiment include a sensor, as described below, the medical observation device 100 performs a process related to the processing method according to this embodiment using a detection result of the sensor.

Figure 2:
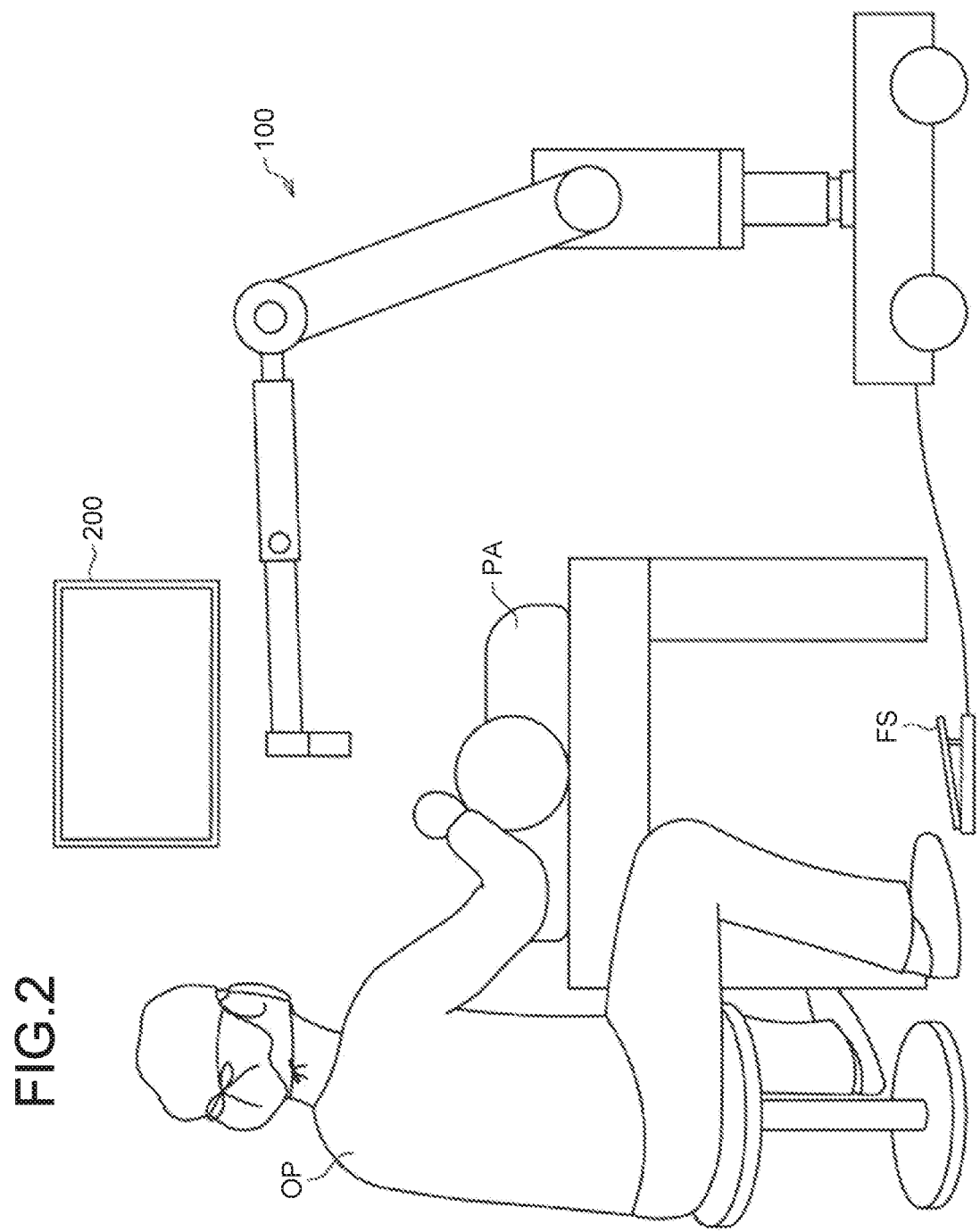
FIG. 2 is an explanatory diagram illustrating an example of a use case where the medical observation system according to this embodiment is used.

FIG. 2 is an explanatory diagram illustrating an example of a use case where the medical observation system 1000 according to this embodiment is used.

A patient PA (a target patient who receives a medical service) of the observation target is captured by an imaging device (described below) of the medical observation device 100. In the following, an image captured by the medical observation device according to this embodiment (for example, a captured image of the patient who is a subject to be received the medical service) will be denoted as "medical captured image".

The medical captured image captured by the medical observation device 100 is displayed in the display screen of the display device 200. Then, an operator OP (an example of a user of the medical observation device 100) who performs the medical service using the medical observation device 100 performs the medical service on the patient PA while viewing the medical captured image displayed in the display screen of the display device 200.

In addition, the operator OP operates an external operation device of the medical observation device 100 such as a foot switch FS, or the operation device (described below) of the medical observation device 100 to operate an arm (described below) and an imaging device (described below) of the medical observation device 100 so as to set the medical observation device 100 to a desired state. In addition, the operator OP can change one or both of an imaging operation of the imaging device (described below) of the medical observation device 100 and a display of the medical captured image which is captured in the imaging device (described below) by operating the operation device 300 (not illustrated) as described below.

Figure 3:
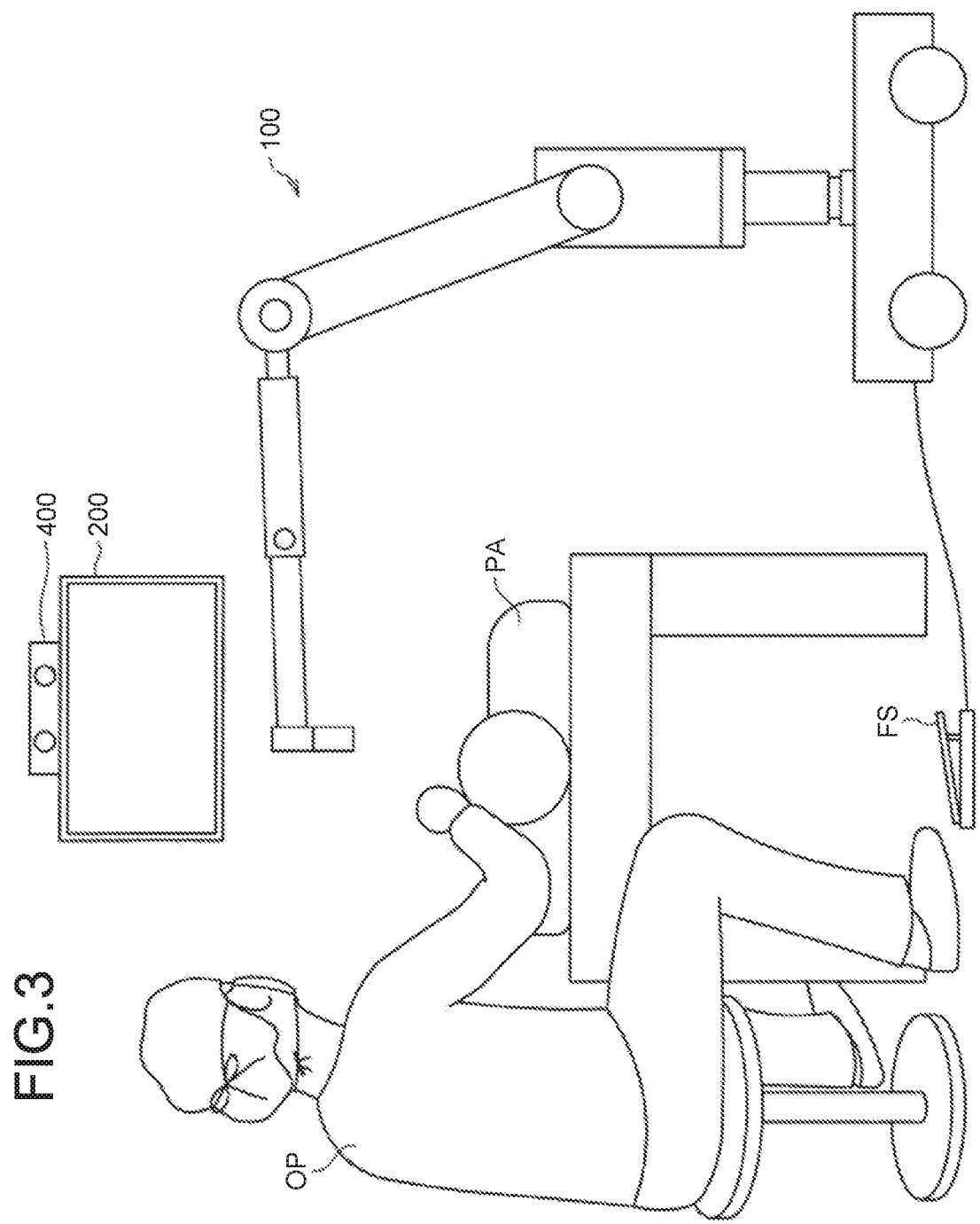
FIG. 3 is an explanatory diagram of another example of the use case where the medical observation system according to this embodiment is used.

FIG. 3 is an explanatory diagram of another example of the use case where the medical observation system 1000 according to this embodiment is used. FIG. 3 illustrates a use case in a case where the medical observation system 1000 further includes a sensor 400.

In a case where the medical observation system 1000 includes the line-of-vision detecting sensor as the sensor 400, for example, the line of vision of the operator OP is detected by the sensor 400. The medical observation device 100 performs a process corresponding to the line of vision recognized, for example, based on the detection result output from the sensor 400 to operate the arm (described below). In other words, in a case where the medical observation system 1000 further includes the line-of-vision detecting sensor, the operator OP changes a position of the imaging device (described below) according to the line of vision, and can set the medical observation device 100 to a desired state.

In a case where the medical observation system 1000 includes the motion detecting sensor as the sensor 400, for example, the motion of the operator OP is detected by the sensor 400. The medical observation device 100 performs a process corresponding to the motion recognized, for example, based on the detection result output from the sensor 400 to operate one or both of the arm (described below) and the imaging device (described below). In other words, in a case where the medical observation system 1000 further includes the motion detecting sensor, the operator OP can set the medical observation device 100 to a desired state by motion.

Hereinbelow, devices of the medical observation system 1000 will be described. In addition, in the following, the sensor of the medical observation system 1000 will be described by taking an example of "a sensor unit which includes the stereo camera and the processor, and detects one or both of the line of vision and the motion from the image captured by the stereo camera". The sensor is "the sensor 400" or "the sensor unit which includes the stereo camera".

[1-1] Display Device 200

The display device 200 is a display means in the medical observation system 1000, and corresponds to an external display device when viewed from the medical observation device 100. The display device 200 displays various image, for example, the medical captured image (moving image, or a plurality of still images; hereinbelow, the same shall apply.) captured in the medical observation device 100, an image related to a UI (User Interface) in the display screen. In addition, the display device 200 may be configured to display a 3D image. The display in the display device 200 is controlled by, for example, the medical observation device 100 or the control device (not illustrated).

The display device 200 in the medical observation system 1000 is installed in any place such as a wall, a ceiling, and a floor of an operating room where a person related to a surgical operation such as an operator can view in the operating room. Examples of the display device 200 include a liquid crystal display, an organic EL (Electro-Luminescence) display, and a CRT (Cathode Ray Tube) display.

Further, the display device 200 is not limited to the above examples.

For example, the display device 200 may be any wearable device such as a head mounted display and an eyewear device with which the operator wears on his/her body.

The display device 200 is driven by power supplied from an internal power source such as a battery of the display device 200, or power supplied from an external power source connected thereto.

[1-2] Operation Device 300

The operation device 300 is an external operation device of the medical observation device 100, and is configured to include a mouth switch (a switch which is pressed by a mouth). The operation device 300 is driven by power supplied from an internal power source such as a battery of the operation device 300, or power supplied from an external power source connected thereto. The operation device 300 is used by a medical worker such as an operator, an assistant of the operator, and a nurse.

The medical worker who uses the operation device 300 bites the mouth switch of the operation device 300 to press the mouth switch. In the following, an operation on the mouth switch of the operation device 300 may indicate "a pressing operation" or "an operation on the mouth switch".

If the pressing operation is performed, the operation device 300 outputs an operation signal according to the pressing operation in a wireless manner (or a wired manner). The medical observation device 100 acquiring the operation signal output from the operation device 300 performs a process related to the processing method (described below) according to this embodiment, and controls the imaging operation of the imaging device (described below) of the medical observation device 100 based on the operation signal.

Therefore, the medical worker who uses the operation device 300 performs the pressing operation using the operation device 300, and thus can change the operation of the medical observation device 100 such as the imaging operation of the imaging device (described below) of the medical observation device 100.

FIG. 4 is an explanatory diagram for describing an example of the operation device 300 according to this embodiment. FIG. 4 illustrates an example of the operation device 300 with which is mounted on the head of the medical worker such as the operator.

The operation device 300 includes a mouth switch 302. The mouth switch 302 is provided at a position where the medical worker can bite the mouth switch 302 when wearing as illustrated in A of FIG. 4.

Further, A of FIG. 4 illustrates an example that the operation device 300 is mounted on the ear of the medical worker. However, the configuration of the operation device 300 is not limited to the example of A of FIG. 4. For example, the operation device 300 may be configured to be mounted on the head of the medical worker like a head phone.

As illustrated in B of FIG. 4, the mouth switch 302 includes, for example, a first operation member 310 and a second operation member 312 which performs the pressing operation when bitten by the medical worker, and an output member 314 which transmits the operation signal according to the pressing operation on the first operation member 310 and the second operation member 312.

For example, the first operation member 310 and the second operation member 312 are provided in parallel (or almost parallel) with a gap therebetween as illustrated in B of FIG. 4. The gap between the first operation member 310 and the second operation member 312 becomes narrow when bitten by the medical worker.

Further, in B of FIG. 4, the first operation member 310 and the second operation member 312 each are formed in a circular shape. However, the shapes of the first operation member 310 and the second operation member 312 are not limited to the example illustrated in B of FIG. 4. For example, the first operation member 310 and the second operation member 312 each may be formed in an arbitrary shape such as a rectangular shape.

The output member 314 is configured to include, for example, a switch (not illustrated), a signal generating circuit (not illustrated), and a communication device (not illustrated).

The switch (not illustrated) of the output member 314 is connected each of the first operation member 310 and the second operation member 312, and the contact point thereof is shorted by the pressing operation to be an ON state (conductive state). In addition, when the pressing operation is not performed, the contact point of the switch (not illustrated) of the output member 314 is released, and the switch (not illustrated) of the output member 314 enters an OFF state (non-conductive state).

The signal generating circuit (not illustrated) of the output member 314 generates the operation signal according to the state of the switch (not illustrated) of the output member 314. The signal generating circuit (not illustrated) of the output member 314 generates a pulse signal of a predetermined pulse width as the operation signal, for example, when the switch (not illustrated) enters the ON state. The pulse width of the operation signal generated by the signal generating circuit (not illustrated) of the output member 314 may be constant, or may vary according to a period when the switch (not illustrated) of the output member 314 enters the ON state. Further, the operation signal generated by the signal generating circuit (not illustrated) of the output member 314 is not limited to the pulse signal. However, any signal may be employed as long as the medical observation device 100 can recognize that the pressing operation is performed (or that the medical observation device 100 identifies the type of the pressing operation as described below).

The communication device (not illustrated) of the output member 314 performs a role of communicating with an external device such as the medical observation device 100 in a wireless or wired manner. If the operation signal is transferred from the signal generating circuit (not illustrated), the communication device (not illustrated) of the output member 314 transmits the transferred operation signal.

In addition, the communication device (not illustrated) of the output member 314 may transmit the operation signal and identification information (for example, an ID indicating the operation device 300) with which the external device can specify the operation device 300. The communication device (not illustrated) of the output member 314 transmits the identification information together with the operation signal, so that the medical observation device 100 receiving the operation signal can specify the operation device 300 on which the pressing operation is performed.

Herein, examples of the communication device (not illustrated) of the output member 314 include IEEE802.15.1 port and a transmitting/receiving circuit (wireless communication), IEEE802.11 port and a transmitting/receiving circuit (wireless communication), a communication antenna and an RF (Radio Frequency) circuit (wireless communication), or a LAN (Local Area Network) terminal and a transmitting/receiving circuit (wired communication). The communication device (not illustrated) is configured to perform the communication in a manner corresponding to the communication device (described below) of the medical observation device 100 or in a manner corresponding to the communication device connected to the medical observation device 100.

The operation device 300 is configured as illustrated with reference to FIG. 4. Further, the configuration of the operation device 300 is not limited to the above example.

Figure 5:
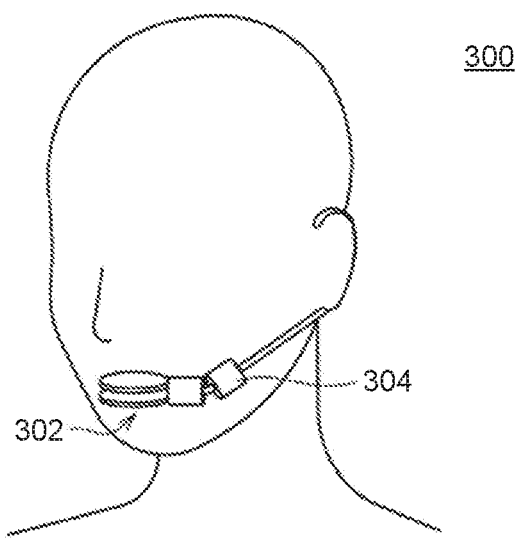
FIG. 5 is an explanatory diagram for describing another example of the operation device according to this embodiment.

FIG. 5 is an explanatory diagram for describing another example of the operation device 300 according to this embodiment. Similarly to FIG. 4, FIG. 5 illustrates an example of the operation device 300 with which the medical worker such as the operator wears on his/her head.

The operation device 300 illustrated in FIG. 5 further includes a voice input device 304 such as a microphone in addition to the configuration of the operation device 300 illustrated in FIG. 4. The voice input device 304 generates, for example, a voice signal such as a voice signal according to a voice uttered by the medical worker who wears the operation device 300.

The voice input device 304 is electrically connected to the communication device (not illustrated) of the output member 314. The voice signal generated by the voice input device 304 is transferred to the communication device (not illustrated). Then, the voice signal generated by the voice input device 304 is output by communication in the communication device (not illustrated). The medical observation device 100 acquiring the voice signal output from the operation device 300 performs a process related to the processing method (described below) according to this embodiment, and controls the imaging operation of the imaging device (described below) of the medical observation device 100 based on the voice signal.

[1-3] Medical Observation Device 100

The medical observation device 100 is an electronic medical observation device. For example, in a case where the medical observation device 100 is used at the time of a surgical operation, the operator (an example of the user of the medical observation device 100) observes an operation site while referring to the medical captured image which is captured by the medical observation device 100 and is displayed in the display screen of the display device 200, and performs various treatments such as a surgery according to a surgical method on the operation site.

First, an example of a hardware configuration of the medical observation device 100 will be described with reference to FIG. 1.

The medical observation device 100 includes, for example, a base 102, an arm 104, and an imaging device 106.

In addition, while not illustrated in FIG. 1, the medical observation device 100 may include, for example, one or two or more processors (not illustrated) configured by a calculation circuit such as an MPU (Micro Processing Unit), a ROM (Read Only Memory; not illustrated), a RAM (Random Access Memory; not illustrated), a storage medium (not illustrated), and a communication device (not illustrated). The medical observation device 100 is driven by power supplied from an internal power source such as a battery of the medical observation device 100, or power supplied from an external power source connected thereto.

The processor (not illustrated) serves as a control unit described below. The ROM (not illustrated) stores a program used by the processor (not illustrated) and control data such as calculation parameters. The RAM (not illustrated) temporarily stores the program which is performed by the processor (not illustrated).

The storage medium (not illustrated) serves as a memory unit. The storage medium (not illustrated) stores, for example, data related to the processing method according to this embodiment such as a table (or database) in which the type of the pressing operation and the process to be performed are associated, and various data such as various types of applications. Herein, examples of the storage medium (not illustrated) include a magnetic storage medium such as a hard disk, and a non-volatile memory such as a flash memory. In addition, the storage medium (not illustrated) may be detachable from the medical observation device 100.

The communication device (not illustrated) is a communication means of the medical observation device 100, and performs a role of communicating with an external device such as the display device 200 and the operation device 300 in a wireless or wired manner. Herein, examples of the communication device (not illustrated) include IEEE802.15.1 port and a transmitting/receiving circuit (wireless communication), IEEE802.11 port and a transmitting/receiving circuit (wireless communication), a communication antenna and an RF circuit (wireless communication), a LAN terminal, and a transmitting/receiving circuit (wired communication). The communication device (not illustrated) may be configured to communicate with one or two or more external devices by a plurality of communication methods.

[1-3-1] Base 102

The base 102 is a base of the medical observation device 100, and is connected to one end of the arm 104 to support the arm 104 and the imaging device 106.

In addition, the base 102 is provided with casters, and the medical observation device 100 is grounded to the floor through the casters. With the casters, the medical observation device 100 can easily move on the floor by the casters.

[1-3-2] Arm 104

The arm 104 is configured by a plurality of links which are connected to each other by joint portions.

In addition, the arm 104 supports the imaging device 106. The imaging device 106 supported by the arm 104 is movable three-dimensionally. The position and the posture of the moved imaging device 106 are held by the arm 104.

More specifically, the arm 104 is configured by, for example, a plurality of joint portions 110*a*, 110*b*, 110*c*, 110*d*, 110*e*, and 110*f* and a plurality of links 112*a*, 112*b*, 112*c*, 112*d*, 112*e*, and 112*f* which are rotatably connected to each other by the joint portions 110*a*, 110*b*, 110*c*, 110*d*, 110*e*, and 110*f*. A rotatable range of each of the joint portions 110*a*, 110*b*, 110*c*, 110*d*, 110*e*, and 110*f* is arbitrarily set in a design stage or a manufacturing stage to realize a desired motion of the arm 104.

In other words, in the medical observation device 100 illustrated in FIG. 1, six degrees of freedom in movement of the imaging device 106 are realized by six rotation axes (a first axis O1, a second axis O2, a third axis O3, a fourth axis O4, a fifth axis O5, and a sixth axis O6) corresponding to six joint portions 110*a*, 110*b*, 110*c*, 110*d*, 110*e*, and 110*f* of the arm 104. More specifically, the motions of the six degrees of freedom (three degrees of freedom in translation and three degrees of freedom in rotation) are realized in the medical observation device 100 illustrated in FIG. 1.

Each of the joint portions 110a, 110b, 110c, 110d, 110e, and 110f is provided with an actuator (not illustrated), and each of the joint portions 110a, 110b, 110c, 110d, 110e, and 110f rotates about the corresponding rotation axis by the driving of the actuator (not illustrated). The driving of the actuator (not illustrated) is controlled by, for example, a processor serving as the control unit described below or an external control device (not illustrated).

Each of the joint portions 110a, 110b, 110c, 110d, 110e, and 110f rotates about the corresponding rotation axis by the driving of the actuator (not illustrated), so that various operations of the arm 104 such as expanding or contracting (folding) of the arm 104 are realized.

The joint portion 110a is formed in a substantially columnar shape, and is supported by a distal end (the lower end portion in FIG. 1) of the joint portion 110a such that the imaging device 106 (the upper end portion of the imaging device 106 in FIG. 1) is rotatable about the rotation axis (the first axis O1) which is parallel with the center axis of the imaging device 106. Herein, the medical observation device 100 is configured to match the first axis O1 with an optical axis in the imaging device 106. In other words, the imaging device 106 rotates about the first axis O1 illustrated in FIG. 1, so that the medical captured image captured by the imaging device 106 becomes an image which is changed as if the visual field rotates.

The link 112a is a member of a substantially rod shape, and fixedly supports the joint portion 110a. The link 112a extends in a direction perpendicular to the first axis O1 for example, and is connected to the joint portion 110b.

The joint portion 110b is formed in a substantially columnar shape, and supports the link 112a to be rotatable about the rotation axis (the second axis O2) perpendicular to the first axis O1. In addition, the joint portion 110b is fixedly connected to the link 112b.

The link 112b is a member of a substantially rod shape, and extends in a direction perpendicular to the second axis O2. In addition, the link 112b is connected to each of the joint portion 110b and the joint portion 110c.

The joint portion 110c is formed in a substantially columnar shape, and supports the link 112b to be rotatable about the rotation axis (the third axis O3) perpendicular to each of the first axis O1 and the second axis O2. In addition, the joint portion 110c is fixedly connected to one end of the link 112c.

Herein, the distal end side (the side where the imaging device 106 is provided) of the arm 104 rotates about the second axis O2 and the third axis O3, so that the imaging device 106 can move such that the position of the imaging device 106 is changed in a horizontal plane. In other words, the rotations about the second axis O2 and the third axis O3 are controlled in the medical observation device 100, so that the visual field of the medical captured image can move in a horizontal plane.

The link 112c is a member of which one end is formed in a substantially columnar shape, and the other end is formed in a substantially rod shape. On one end side of the link 112c, the center axis of the joint portion 110c and the center axis of the substantially columnar shape are fixedly connected to be equal. In addition, the joint portion 110d is connected to the other end side of the link 112c.

The joint portion 110d is formed in a substantially columnar shape, and supports the link 112c to be rotatable about the rotation axis (the fourth axis O4) perpendicular to the third axis O3. The joint portion 110d is fixedly connected to the link 112d.

The link 112d is a member of a substantially rod shape, and extends to be perpendicular to the fourth axis O4. One end of the link 112d is fixedly connected to the joint portion 110d to abut on the side surface of the substantially columnar shape of the joint portion 110d. In addition, the joint portion 110e is connected to the other end (the end on the opposite side to a portion where the joint portion 110d is connected) of the link 112d.

The joint portion 110e is formed in a substantially columnar shape, and supports one end of the link 112d to be rotatable about the rotation axis (the fifth axis O5) which is parallel to the fourth axis O4. In addition, the joint portion 110e is fixedly connected to one end of the link 112e.

Herein, the fourth axis O4 and the fifth axis O5 are the rotation axes on which the imaging device 106 can move in a vertical direction. The distal end side (the side where the imaging device 106 is provided) of the arm 104 rotates about the fourth axis O4 and the fifth axis O5, so that the position in the vertical direction of the imaging device 106 is changed. Therefore, the distal end side (the side where the imaging device 106 is provided) of the arm 104 rotates about the fourth axis O4 and the fifth axis O5, so that a distance between the imaging device 106 and an observation target (the operation site of the patient) can be changed.

The link 112e is a member configured by combining a first member which is formed in a substantially L shape such that one side extends in the vertical direction and the other side extends in the horizontal direction, and a second member of a rod shape extending in a vertically downward direction from the portion which extends in the horizontal direction of the first member. The joint portion 110e is fixedly connected to the portion extending in the vertical direction of the first member of the link 112e. In addition, the joint portion 110f is connected to the second member of the link 112e.

The joint portion 110f is formed in a substantially columnar shape, and supports the link 112e to be rotatable about the rotation axis (the sixth axis O6) which is parallel to the vertical direction. In addition, the link 112f is fixedly connected to the joint portion 110f.

The link 112f is a member formed in a substantially rod shape, and extends in the vertical direction. One end of the link 112f is connected to the joint portion 110f. In addition, the other end (the end on the opposite side to a portion where the joint portion 110f is connected) of the link 112f is fixedly connected to the base 102.

With the above configuration of the arm 104, the six degrees of freedom in movement of the imaging device 106 is realized in the medical observation device 100.

Further, the configuration of the arm 104 is not limited to the above example.

For example, a brake may be provided in each of the joint portions 110a, 110b, 110c, 110d, 110e, and 110f of the arm 104 to regulate the rotation of each of the joint portions 110a, 110b, 110c, 110d, 110e, and 110f. Examples of the brake according to this embodiment include any type of brake such as an electrically driven brake or a magnetic brake which is driven magnetically.

The driving of the brake is controlled by, for example, a processor serving as the control unit described below or an external control device (not illustrated). Since the driving of the brake is controlled, the medical observation device 100 is set with an operation mode of the arm 104. Examples of the operation mode of the arm 104 include a fix mode and a free mode.

Herein, the fix mode according to this embodiment is an operation mode in which, for example, the rotation in each rotation axis provided in the arm 104 is regulated by the brake so that the position and the posture of the imaging device 106 are fixed. When the arm 104 is set to the fix mode, the operation state of the medical observation device 100 becomes a fixed state in which the position and the posture of the imaging device 106 are fixed.

In addition, the free mode according to this embodiment is an operation mode in which the brake is released and each rotation axis provided in the arm 104 freely rotates. For example, in the free mode, the position and the posture of the imaging device 106 can be adjusted by an operator's direct operation. Herein, the direct operation according to this embodiment means, for example, that the operator grips the imaging device 106 by hand and directly moves and operates the imaging device 106.

[1-3-3] Imaging Device 106

The imaging device 106 is supported by the arm 104, and captures an observation target such as the operation site of the patient. The capturing in the imaging device 106 is controlled by, for example, a processor serving as the control unit described below or an external control device (not illustrated).

The imaging device 106 is configured to correspond to an electronic microscope for example.

Figure 6:
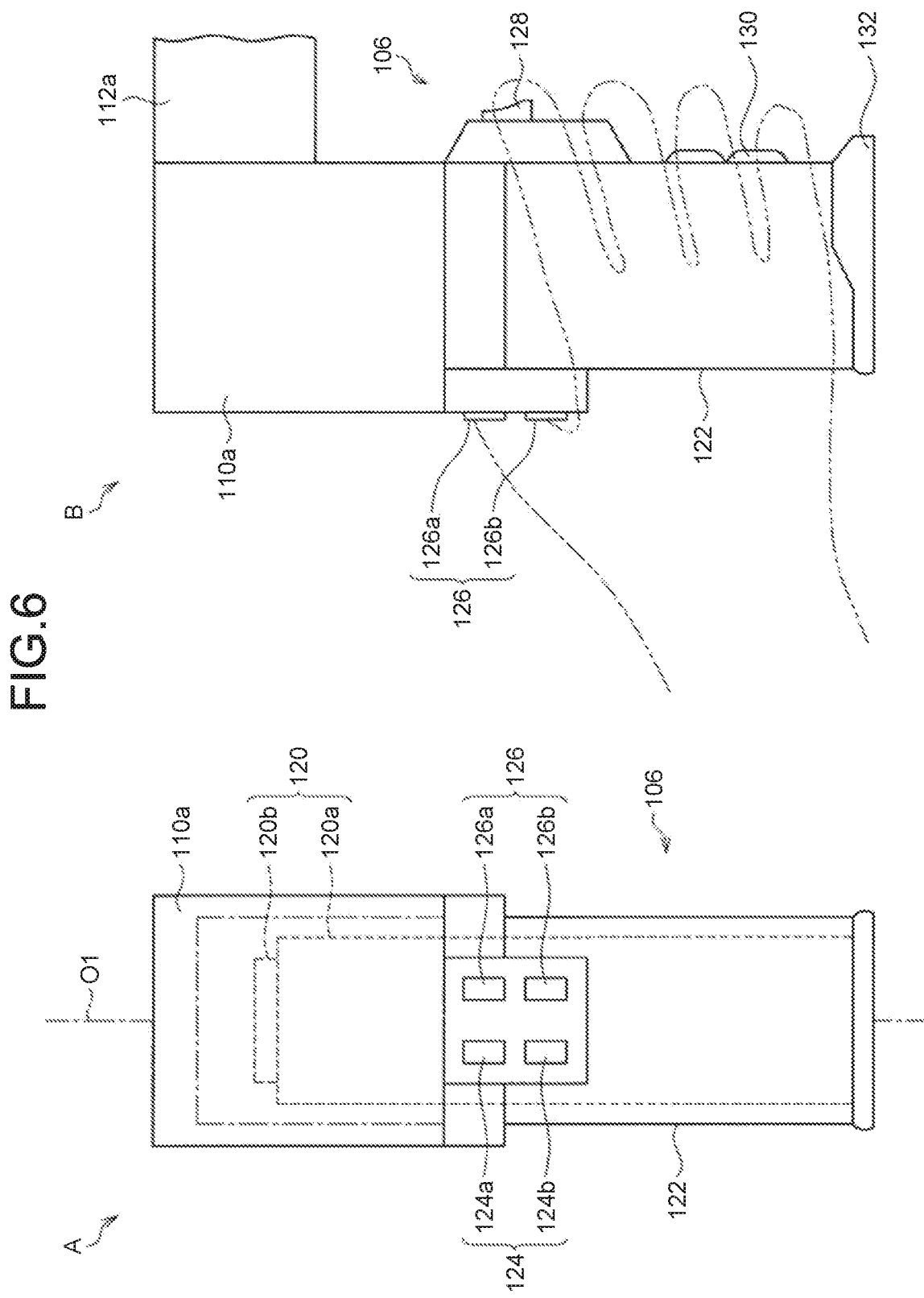
FIG. 6 is an explanatory diagram for describing an example of the configuration of an imaging device of a medical observation device according to this embodiment.

FIG. 6 is an explanatory diagram for describing an example of the configuration of the imaging device 106 of the medical observation device 100 according to this embodiment.

The imaging device 106 includes, for example, an imaging member 120 and a cylindrical member 122 of a substantially cylindrical shape. The imaging member 120 is provided in the cylindrical member 122.

In an aperture surface at the lower end (the end on the lower side in FIG. 6) of the cylindrical member 122, there is provided a cover glass (not illustrated) to protect the imaging member 120 for example.

In addition, for example, a light source (not illustrated) is provided in the cylindrical member 122. At the time of capturing an image, an illumination light is emitted from the light source to a subject through the cover glass. A reflected light (observation light) from the subject emitted with the illumination light is incident on the imaging member 120 through the cover glass (not illustrated), and an image signal indicating the subject (an image signal indicating the captured image) is obtained by the imaging member 120.

As the imaging member 120, a configuration used in a well-known electronic microscope may be applied.

As an example, the imaging member 120 is configured by, for example, an optical system 120*a* and an image sensor 120*b* which includes an imaging element to capture an image of the observation target by the light passing through the optical system 120*a*. The optical system 120*a* is configured by optical elements such as one or two or more lens and mirrors, for example, an objective lens, a zoom lens, and a focus lens. Examples of the image sensor 120*b* include an image sensor which uses a plurality of imaging elements such as a CMOS (Complementary Metal Oxide Semiconductor) and a CCD (Charge Coupled Device).

The imaging member 120 may be configured to include a pair of imaging elements (that is, so-called stereo camera). The imaging member 120 has one or two or more functions of a well-known electronic microscope such as an AF (Auto Focus) function which includes at least a zoom function (one or both of an optical zoom function and an electronic zoom function).

In addition, the imaging member 120 may be configured to capture an image at 4 K or 8 K (so-called high resolution). Since the imaging member 120 is configured to capture an image at a high resolution, the image can be displayed in the display device 200 having a large display screen (for example, 50 or more inches) while securing a predetermined resolution (for example, Full HD image quality). Therefore, the visibility of the operator who views the display screen is improved. In addition, since the imaging member 120 is configured to capture an image at a high resolution, a predetermined resolution can be secured even when the captured image is magnified by the electronic zoom function and displayed in the display screen of the display device 200. Further, in a case where a predetermined resolution is secured using the electronic zoom function, the performance of the optical zoom function in the imaging device 106 can be restricted. Therefore, the optical system of the imaging device 106 can be made easily, and the imaging device 106 can be further minimized.

In the imaging device 106, for example, various types of operation devices are provided to control the operation of the imaging device 106. For example, in FIG. 6, a zoom switch 124, a focus switch 126, and an operation mode change switch 128 are provided in the imaging device 106. Further, it is a matter of course that the positions and the shapes of the zoom switch 124, the focus switch 126, and the operation mode change switch 128 are not limited to the example illustrated in FIG. 6.

The zoom switch 124 and the focus switch 126 are examples of the operation device to adjust the imaging condition in the imaging device 106.

The zoom switch 124 is configured by, for example, a zoom-in switch 124*a* which increases a zoom magnification (magnification) and a zoom-out switch 124*b* which decreases the zoom magnification. When the operation is performed on the zoom switch 124, the zoom magnification is adjusted, and the zooming is adjusted. In the following, the increasing of the zoom magnification may be referred to as "zoom-in", and the decreasing of the zoom magnification may be referred to as "zoom-out".

The focus switch 126 is configured by, for example, a distant-view focus switch 126*a* which makes a focal length up to the observation target (subject) long, and a close-view focus switch 126*b* which makes the focal length up to the observation target short. When the operation is performed on the focus switch 126, the focal length is adjusted, and the focus is adjusted. In the following, making the focal length up to the observation target long may be referred to as "focus-out", and making the focal length up to the observation target short may be referred to as "focus-in".

The operation mode change switch 128 is an example of the operation device to change the operation mode of the arm 104 in the imaging device 106. When the operation is performed on the operation mode change switch 128, the operation mode of the arm 104 is changed. Examples of the operation mode of the arm 104 include the fix mode and the free mode as described above.

An example of the operations on the operation mode change switch 128 includes an operation of pressing the operation mode change switch 128. For example, during a period when the operator presses the operation mode change switch 128, the operation mode of the arm 104 becomes the free mode. During a period when the operator does not press the operation mode change switch 128, the operation mode of the arm 104 becomes the fix mode.

In addition, the imaging device 106 is provided with an antislip member 130 and a projection member 132 in order to improve operability and convenience when the operator operates various types of operation devices.

The antislip member 130 is, for example, a member which is provided to prevent an operation body from slipping when the operator operates the cylindrical member 122 with the operation body such as a hand. The antislip member 130 is formed of a material of a large friction coefficient, and is structured to hardly slip such as irregularities.

The projection member 132 is a member which is provided to prevent that the operation body blocks the visual field of the optical system 120a when the operator operates the cylindrical member 122 with the operation body such as a hand, or that the cover glass from being unclean by the contact of the operation body with the cover glass (not illustrated) when the operation is performed by the operation body.

Further, it is a matter of course that the positions and the shapes of the antislip member 130 and the projection member 132 are not limited to the example illustrated in FIG. 6. In addition, the imaging device 106 may not be provided with one or both of the antislip member 130 and the projection member 132.

The image signal (image data) generated by the imaging in the imaging device 106 is subjected to image processing in the processor which serves as the control unit described below for example. Examples of the image processing according to this embodiment include one or two or more of various processes such as a gamma correction, a white balance adjustment, expansion or contraction of an image related to the electronic zoom function, or an inter-pixel correction. Further, in a case where the medical observation system according to this embodiment includes the control device which controls various operations in the medical observation device 100, the image processing according to this embodiment may be performed in the control device (not illustrated).

The medical observation device 100 transmits, for example, a display control signal and an image signal subjected to the above image processing to the display device 200.

When the display control signal and the image signal are transmitted to the display device 200, the medical captured image (for example, an image obtained by capturing the operation site) where the observation target is captured is expanded or contracted at a desired magnification by one or both of the optical zoom function and the electronic zoom function in the display screen of the display device 200.

The medical observation device 100 includes, for example, a hardware configurations illustrated with reference to FIGS. 1 and 6.

Further, the hardware configuration of the medical observation device according to this embodiment is not limited to the configurations illustrated in FIGS. 1 and 6.

For example, the medical observation device according to this embodiment may not include the base 102, and be configured such that the arm 104 is directly attached to a ceiling or a wall of the operating room. For example, in a case where the arm 104 is attached to the ceiling, the medical observation device according to this embodiment is configured such that the arm 104 is suspended from the ceiling.

In addition, FIG. 1 illustrates an example that the arm 104 is configured to realize the six degrees of freedom in driving the imaging device 106. However, the configuration of the arm 104 is not limited to the configuration that the degree of freedom in driving the imaging device 106 becomes the six degrees of freedom. For example, the arm 104 may be configured to appropriately move the imaging device 106 according to applications. The number and the layout of the joint portions and the links, and the direction of driving axis of the joint portion may be appropriately set for a desired degree of freedom of the arm 104. As an example, the medical observation device according to this embodiment may be configured simpler than the X and Y axes control like a microscope for ophthalmology.

In addition, FIGS. 1 and 6 illustrate examples that various types of operation devices for controlling the operation of the imaging device 106 are provided in the imaging device 106. However, some or all of the operation devices illustrated in FIGS. 1 and 6 may be provided in the imaging device 106. As an example, various types of operation devices for controlling the operation of the imaging device 106 may be provided in a place other than the imaging device 106 of the medical observation device according to this embodiment. In addition, as another example, various types of operation devices for controlling the operation of the imaging device 106 may be an external operation device such as the foot switch or a remote controller. In addition, as described below, the operation of the imaging device 106 is controlled even by the operation device 300.

Figure 7:
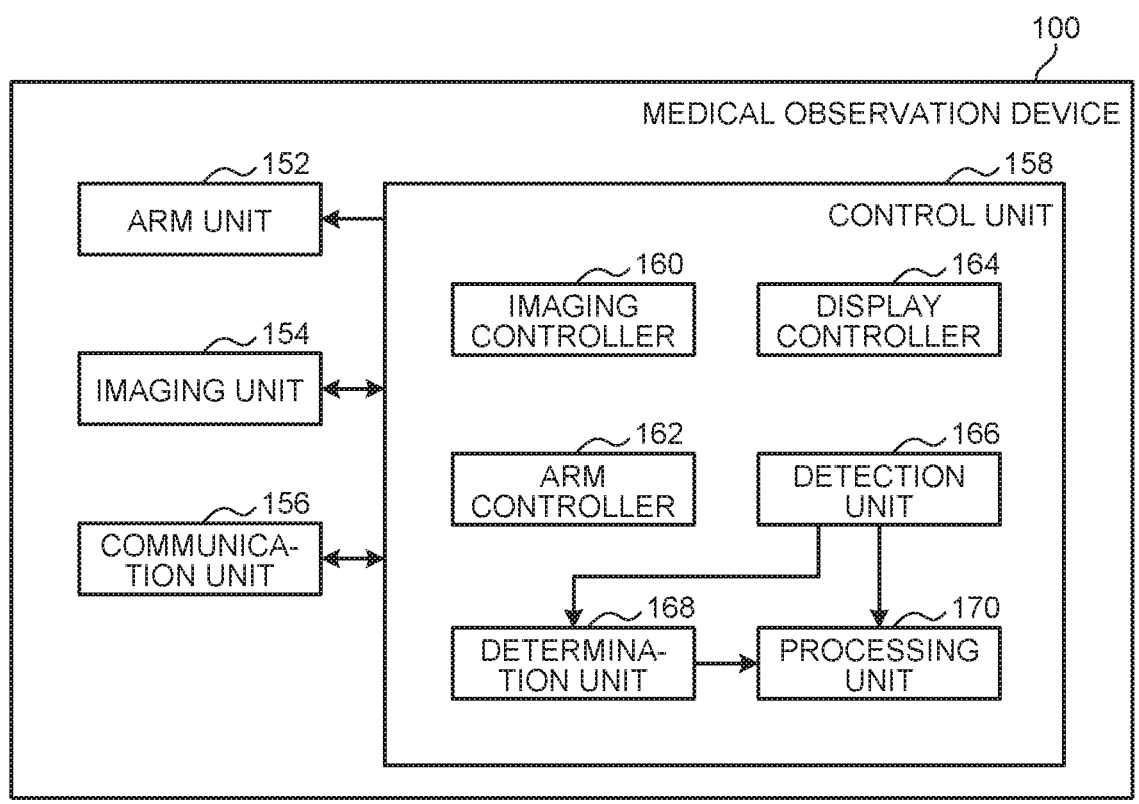
FIG. 7 is a functional block diagram illustrating an example of the configuration of the medical observation device according to this embodiment.

Next, the medical observation device 100 illustrated in FIG. 1 will be described using functional blocks. FIG. 7 is a functional block diagram illustrating an example of the configuration of the medical observation device 100 according to this embodiment.

The medical observation device 100 includes, for example, an arm unit 152, an imaging unit 154, a communication unit 156, and a control unit 158.

[1-3-4] Arm Unit 152

The arm unit 152 is configured by the arm 104, and supports the imaging device 106 of the imaging unit 154.

[1-3-5] Imaging Unit 154

The imaging unit 154 is configured by the imaging device 106, and captures an image of the observation target. The capturing of the imaging unit 154 is controlled by the control unit 158 for example.

[1-3-6] Communication Unit 156

The communication unit 156 is a communication means of the medical observation device 100, and performs a role of communicating with an external device such as the display device 200 and the operation device 300 in a wireless or wired manner. The communication unit 156 is configured by, for example, the communication device (not illustrated). The communication in the communication unit 156 is controlled by the control unit 158 for example.

[1-3-7] Control Unit 158

The control unit 158 is configured by, for example, the processor (not illustrated), and performs a role of controlling the entire medical observation device 100. In addition, the control unit 158 performs a leading role of performing a process related to the processing method described below. Further, the process related to the processing method in the control unit 158 may be performed by being distributed to a plurality of processing circuits (for example, a plurality of processors).

More specifically, the control unit 158 includes, for example, an imaging controller 160, an arm controller 162, a display controller 164, a detection unit 166, a determination unit 168, and a processing unit 170. Further, as described below, the control unit 158 may be configured to include no determination unit 168.

[1-3-7-1] Imaging Controller 160

The imaging controller 160 controls the imaging device 106 of the imaging unit 154. Examples of the control of the imaging device 106 include the controls of at least the zoom function (one or both of the optical zoom function and the electronic zoom function), and the control of one or two or more functions of the typical electronic microscope such as the control of the AF function.

In addition, the imaging controller 160 may be configured as the processing unit 170 described below. In a case where the imaging controller serves as the processing unit 170, the imaging controller 160 controls the imaging operation in the imaging device 106 in conjunction with the determination unit 168 described below or the detection unit 166 described below.

[1-3-7-2] Arm Controller 162

The arm controller 162 controls the driving of the arm 104 of the arm unit 152. An example of the control of driving the arm 104 includes "applying a control signal to the actuator (not illustrated) corresponding to each of the joint portions 110a, 110b, 110c, 110d, 110e, and 110f so as to control the driving".

In addition, the arm controller 162 may serve as the processing unit 170 described below. In a case where the arm controller 162 serves as the processing unit 170, the arm controller 162 controls the determination unit 168 described below, or the detection unit 166 and the driving of the arm 104 described below.

[1-3-7-3] Display Controller 164

The display controller 164 transmits, for example, the display control signal and the image signal to the communication device (not illustrated) of the communication unit 156, and transmits the display control signal and the image signal to the display device 200 so as to control the display in the display device 200. Further, the controlling of the communication in the communication unit 156 may be performed by a communication control unit (not illustrated) of the control unit 158.

In addition, the display controller 164 may serve as the processing unit 170 described below. In a case where the display controller 164 serves as the processing unit 170, the display controller 164 controls the determination unit 168 described below, or the detection unit 166 and the display (the display of the medical captured image captured in the imaging device 106) of the medical captured image in the display device 200.

[1-3-7-4] Detection Unit 166

The detection unit 166 performs a role of performing the detection process in the process related to the processing method according to this embodiment, and detects the pressing operation based on the operation signal corresponding to the pressing operation on the mouth switch which is output from the operation device 300 (an example of the external operation device equipped with the mouth switch; the same shall apply hereafter).

The medical observation device 100 detects, for example, a specific signal pattern from the operation signal transmitted from the operation device 300 so as to detect the pressing operation on the mouth switch. Taking a case where the operation signal is the pulse signal as an example, the detection unit 166 determines that the pressing operation on the mouth switch is detected when a pulse (an example of a specific signal pattern). The determination on whether a pressing operation on the mouth switch is detected corresponds to a determination on whether the operation signal transmitted from the operation device 300 is acquired.

The detection result of the detection unit 166 is transferred to, for example, the determination unit 168 and the processing unit 170. In each of the determination unit 168 and the processing unit 170, the process is performed by being triggered at the detection of the pressing operation.

In a case where the control unit 158 does not include the determination unit 168, the detection result in the detection unit 166 is transferred to the processing unit 170. In this case, the processing unit 170 performs a process corresponding to the pressing operation by being triggered at the detection of the pressing operation.

[1-3-7-5] Determination Unit 168

The determination unit 168 performs a role of performing a determination process in the process related to the processing method according to this embodiment, and determines a process corresponding to the detected pressing operation based on the operation signal according to the pressing operation to the mouth switch which is detected from the operation device 300.

Herein, examples of the process corresponding to the pressing operation according to this embodiment include some or all of "a process related to the imaging operation of the imaging device 106", "a process related to a display of the medical captured image which is captured in the imaging device 106", and "an identification process".

As a process related to the imaging operation of the imaging device 106, there is a process of directly changing the imaging operation of the imaging device 106. Examples of the process of directly changing the imaging operation of the imaging device 106 include one or two or more processes among "a process of changing the zoom magnification such as zoom-in and zoom-out", "a process of adjusting a focus position such as focus-in and focus-out", "a process of changing an imaging position by driving the arm 104 to move the imaging device 106", "a process of changing a focal depth such as changing a diaphragm value of a lens", and "a process of changing an observation mode". In other words, examples of the process related to the imaging operation of the imaging device 106 include one or two or more processes of changing the zoom magnification, adjusting the focus position, changing the imaging position, changing the focal depth, and changing the observation mode.

Examples of the observation mode according to this embodiment include one or two or more special light observation modes, and a natural light observation mode. The special light observation mode is an observation mode in which the imaging is performed using a special light (a light of a specific wavelength bandwidth). Examples of the special light observation mode include a fluorescence observation mode in which the imaging is performed using a light of in a near-infrared wavelength bandwidth, and a fluorescence observation mode in which the imaging is performed using a light of a fluorescence wavelength bandwidth for observing fluorescence with 5-ALA. In addition, the natural light observation mode is an observation mode in which the imaging is performed using a natural light.

In a case where the determination unit 168 determines a process related to the imaging operation of the imaging device 106 as a process corresponding to the pressing operation, the processing unit 170 described below performs the process related to the imaging operation of the imaging device 106. In the processing unit 170 described below, the process related to the imaging operation of the imaging device 106 is performed as the process corresponding to the pressing operation so as to change the imaging operation of the imaging device 106 which includes one or two or more processes among the changing of the zoom magnification, the adjusting of the focus position, the changing of the imaging position, the changing of the focal depth, and the changing of the observation mode.

As a process related to a display of the medical captured image which is captured in the imaging device 106, for example, there is a process of directly changing a display mode of the medical captured image. An example of the process of changing the display mode of the medical captured image includes one or both of "a process of changing the display mode of the screen" and "a process of changing a color mode". In other words, the process related to the display of the medical captured image includes one or both of the changing of the display mode of the screen and the changing of the color mode.

Examples of the display mode of the screen according to this embodiment include a display mode for displaying in a single screen display, and a display mode for displaying in a multi-screen display. In the single screen display, only the medical captured image is displayed in the display screen. An example of the multi-screen display includes a display of a medical captured image and other images in the display screen such as a PIP (Picture In Picture) display and a POP (Picture Out Picture) display.

An example of the color mode according to this embodiment includes a combination of a display color and a display gradation which can be changed in the display device such as the display device 200 where the medical captured image is displayed. In addition, the color mode according to this embodiment may include a display in a gray scale.

In a case where the determination unit 168 determines a process related to the medical captured image as a process corresponding to the pressing operation, the processing unit 170 described below performs a process related to the display of the medical captured image. In the processing unit 170 described below, the process related to the display of the medical captured image is performed as a process corresponding to the pressing operation, so that the specification of the display of the medical captured image containing one or both of the change of the display mode of the screen and the change of the color mode is changed.

The identification process according to this embodiment is a process of identifying a user's input to instruct a process related to the imaging operation or a process related to the display of the medical captured image. Examples of the identification process include a voice recognition process, a line-of-vision recognition process in which the line of vision of a recognition target is recognized, or a motion recognition process in which the motion of the recognition target is recognized.

As a target of the voice recognition process performed in the medical observation device 100, for example, there is a voice signal output from the voice input device 304 of the operation device 300 illustrated in FIG. 5.

As the recognition target in each of the line-of-vision recognition process performed in the medical observation device 100, and the motion recognition process performed in the medical observation device 100, for example, there is an operator of the operation device 300 (an external operation device equipped with the mouth switch). With the operator of the operation device 300 as the recognition target, the medical observation device 100 can perform a process corresponding to a recognition result onto a specific person who operates the operation device 300.

For example, in a case where the sensor 400 is a sensor unit which includes the stereo camera, the medical observation system 1000 specifies the recognition target by performing a predetermined image processing on the captured image such a process of detecting the operation device 300 from the captured image. The predetermined image processing in the medical observation system 1000 may be performed by the sensor 400, or may be performed by the medical observation device 100 (or the control device (not illustrated)).

Further, the recognition target in each of the line-of-vision recognition process performed in the medical observation device 100 and the motion recognition process performed in the medical observation device 100 is not limited to the operator of the operation device 300.

For example, in a case where the sensor 400 is a sensor unit which includes the stereo camera, the medical observation system 1000 may specify the recognition target by performing a face detection process in which a predetermined face is detected from the captured image which is captured in the sensor 400 The face detection process in the medical observation system 1000 may be performed by the sensor 400, or may be performed by the medical observation device 100 (or the control device (not illustrated)).

In a case where the determination unit 168 determines the identification process as a process corresponding to the pressing operation, the processing unit 170 described below transitions to a mode where the identification process is performed so as to perform the identification process. In a case where the processing unit 170 described below performs the identification process, the processing unit 170 performs a process corresponding to a user's input identified by the identification process to control the imaging operation of the imaging device 106, or to control the display of the medical captured image. With the control of the imaging operation of the imaging device 106, for example, the imaging operation of the imaging device 106 which includes one or two or more processes among the changing of the zoom magnification, the adjusting of the focus position, the changing of the imaging position, the changing of the focal depth, and the changing of the observation mode is changed. In addition, with the control of the display of the medical captured image, for example, the display mode of the medical captured image which includes one or both of the changing of the display mode of the screen and the changing of the color mode is changed. In other words, the identification process can be described as "a process capable of indirectly performing one or both of the changing of the imaging operation of the imaging device 106 and the changing of the display mode of the medical captured image according to the result of the identification process".

As described above, in each of the determination unit 168 and the processing unit 170, the process is performed by being triggered at the detection of the pressing operation in the detection unit 166. In addition, as described below, the processing unit 170 performs a process determined in the determination unit 168. In other words, in a case where the identification process is determined as a process corresponding to the pressing operation in the determination unit 168, the processing unit 170 transitions to a mode where the identification process based on the detection of the pressing operation is performed, and performs a process corresponding to a user's input identified in the identification process.

The determination unit 168 determines a process associated to the pressing operation as a process associated to the pressing operation. The process associated to the pressing operation may be one or plural.

Herein, in a case where the medical observation device 100 controls a single function based on the operation signal acquired from the operation device 300, the determination unit 168 determines the process associated in advance for the acquisition of the operation signal as a process corresponding to the pressing operation. In a case where a single function is controlled, the determination unit 168 is triggered at the acquisition of the operation signal (the detection of the pressing operation in the detection unit 166), refers to information which is stored in the storage medium such as a memory unit (not illustrated) to define a process, and determines a process corresponding to the pressing operation. As the information to define a process, for example, there is any format of data with which a process to be performed is specified such as the program ID and the program data.

In addition, in a case where the medical observation device 100 controls a plurality of functions based on the operation signal acquired from the operation device 300, the determination unit 168 determines the type of the processing operation based on the operation signal. Then, the determination unit 168 determines a process associated to the determined type of the pressing operation as a process corresponding to the pressing operation.

As the type of the pressing operation, for example, there is a type expressed by the number of times of the pressing operations detected within a predetermined period such as the detection of one time of the pressing operation within the predetermined period during which the type of the operation is determined, and the detection of two times of the pressing operations in the predetermined period. The predetermined period during which the type of the operation is determined may be a fixed period which is set in advance, or may be a variable period which is changeable by an operation of a user (for example, a medical worker such as an operator and an assistant of the operator) who uses the medical observation device 100.

The determination unit 168 counts the number of times of the pressing operations which are performed within the predetermined period by being triggered at the acquisition of the operation signal so as to determine the type of the pressing operation. Making an explanation on a case the operation signal is a pulse signal as an example, the determination unit 168 counts the number of pulses detected within the predetermined period during which the type of the operation is determined, and determines the type of the pressing operation by the number of detected pulses. For example, the determination unit 168 determines the type of the pressing operation by referring "a table (or a database) in which the number of times of the pressing operations (or the number of detected pulses) and the type of the pressing operation are associated" which is stored in the storage medium such as the memory unit (not illustrated).

Further, the determining method of the type of the pressing operation in the determination unit 168 is not limited to the above configuration.

For example, in a case where the operation signal is a pulse signal, the determination unit 168 may determine the type of the pressing operation in consideration of the pulse width of the operation signal. For example, the determination unit 168 determines the type of the pressing operation by referring "a table (or a database) in which the number of detected pulses, the pulse width of the operation signal, and the type of the pressing operation are associated".

The determination result in the determination unit 168 is transferred to the processing unit 170. The processing unit 170 performs a process corresponding to the determination result. In addition, in a case where one or two or more units among the imaging controller 160, the arm controller 162, and the display controller 164 serve as the processing unit 170, the determination result in the determination unit 168 is transferred to each unit serving as the processing unit 170. A process corresponding to the determination result is performed in each unit to which the determination result in the determination unit 168 is transferred.

As described above, the medical observation system according to this embodiment may be configured to include a plurality of operation devices 300. In a case where the medical observation system according to this embodiment includes the plurality of operation devices 300, the determination unit 168 determines a process corresponding to the pressing operation based on the operation signal according to the pressing operation which is output from each of the plurality of operation devices 300. In a case where the determination unit 168 determines a process corresponding to the pressing operation based on the operation signal output from each of the plurality of operation devices 300, the medical observation device 100 operates based on the operation with respect to each of the plurality of operation devices 300.

Further, the process of the determination unit 168 in a case where the medical observation system according to this embodiment includes the plurality of operation devices 300 is not limited to the above example. For example, the determination unit 168 may determine a process corresponding to the pressing operation based on the operation signal according to the pressing operation which is output from some operation devices 300 from among the plurality of operation devices 300.

For example, in a case where the operation device 300 outputs the identification information together with the operation signal, the determination unit 168 specifies the operation device 300 from the acquired identification information. For example, if the operation device 300 is specified, the determination unit 168 determines whether the specified operation device 300 is a target for the determination process based on a priority set to each of the plurality of operation devices 300. For example, the determination unit 168 determines the priority of the specified operation device 300 by referring "a table (or a database) in which the identification information and the priority are associated" which is stored in the storage medium such as the memory unit (not illustrated). For example, the determination unit 168 determines that the operation device 300 with a highest priority or the operation device 300 with a priority equal to or more than a predetermined threshold (or the operation device 300 of which the priority is larger than the threshold) is a target for the determination process. Then, the determination unit 168 determines a process corresponding to the pressing operation based on the operation signal output from the operation device 300 which is determined as a target for the determination process. In addition, the determination unit 168 does not determine a process corresponding to the pressing operation based on the operation signal output from the operation device 300 which is determined as not a target for the determination process.

In a case where the determination unit 168 determines a process corresponding to the pressing operation based on the operation signal output from some operation devices 300 among the plurality of operation devices 300, the medical observation device 100 operates based on the operation with respect to some operation devices 300 among the plurality of operation devices 300.

[1-3-7-6] Processing Unit 170

The processing unit 170 performs a role of performing an execution process in the process related to the processing method according to this embodiment.

For example, the processing unit 170 performs the process corresponding to the pressing operation determined in the determination unit 168 as illustrated in first to fourth examples described in (a) to (d) below.

(a) First Example of Process in Processing Unit 170

For example, in a case where the determination unit 168 determines a process related to the imaging operation of the imaging device 106 as a process corresponding to the pressing operation like the process of changing the zoom magnification, the processing unit 170 performs the process related to the determined imaging operation of the imaging device 106.

(b) Second Example of Process of Processing Unit 170

For example, in a case where the determination unit 168 determines a process related to the display of the medical captured image like the process of changing the display mode of the screen as a process corresponding to the pressing operation, the processing unit 170 performs the determined process related to the display of the medical captured image.

(c) Third Example of Process of Processing Unit 170

For example, in a case where the determination unit 168 determines the identification process as a process corresponding to the pressing operation, the processing unit 170 transitions to a mode to perform the identification process based on the detection of the pressing operation. Then, the processing unit 170 performs a process corresponding to a user's input identified by the identification process. As described above, examples of the identification process include the voice recognition process, the line-of-vision recognition process, and the motion recognition process.

(c-1) Execution of Voice Recognition Process as Identification Process

The processing unit 170 performs the voice recognition process on the voice signal output from the voice input device, and performs a process corresponding to a recognized voice input as a process corresponding to a user's input identified by the identification process. For example, the processing unit 170 performs the voice recognition process on the voice signal, and specifies a command corresponding to the recognized voice. Then, the processing unit 170 performs a process corresponding to the specified command as a process corresponding to the recognized voice input. In the following, a command corresponding to a voice may be referred to as "voice command".

Herein, as an example of the voice input device outputting the voice signal to the target which is subjected to the voice recognition process, there is the voice input device 304 illustrated in FIG. 5. The medical observation device 100 can perform a process corresponding to a command specified from a voice of a specific person who operates the operation device 300 by performing the voice recognition process on the voice signal output from the voice input device 304.

Further, it is a matter of course that the voice input device outputting the voice signal of the target which is subjected to the voice recognition process is not limited to the voice input device 304 illustrated in FIG. 5.

(c-2) Execution of Line-of-Vision Recognition Process as Identification Process

The processing unit 170 performs the line-of-vision recognition process, and performs a process corresponding to a recognized line-of-vision input as a process corresponding to a user's input identified in the identification process. For example, the processing unit 170 performs the process corresponding to the recognized line-of-vision input based on the detection result detected from the line-of-vision detecting sensor such as the sensor 400 as a process corresponding to the recognized line of vision.

As the process corresponding to the recognized line of vision based on the detection result output from the line-of-vision detecting sensor, for example, there is a process of moving the imaging device 106 according to the recognized line of vision. As an example, the processing unit 170 performs "a process in which, when the line of vision moves on the display screen of the display device 200 displayed by the medical captured image, the arm 104 is controlled to display the portion of the medical captured image corresponding to the position of the line of vision at the center position of the display screen so as to move the imaging device 106". Further, the example of the process corresponding to the recognized line of vision based on the detection result output from the line-of-vision detecting sensor is not limited to the above example. However, the processing unit 170 can perform an arbitrary process using the detection result output from the line-of-vision detecting sensor.

(c-3) Execution of Motion Recognition Process as Identification Process

The processing unit 170 performs the motion recognition process, and performs a process corresponding to a recognized motion input as a process corresponding to a user's input identified in the identification process. For example, the processing unit 170 specifies a command corresponding to the recognized motion based on the detection result output from the motion detecting sensor. Then, the processing unit 170 performs a process corresponding to the specified command as a process corresponding to the recognized motion input.

As the motion recognition process performed in the medical observation device 100, for example, there are one or both of a movement recognition process of recognizing the movement of the recognition target, and a gesture recognition process of recognizing the gesture of the recognition target.

As the movement recognition process, for example, there is "a process of recognizing the movement of a part of the recognition target (a face movement of the recognition target) from the detection result output from the motion detecting sensor" or "a process of recognizing the movement of the entire recognition target from the detection result output from the motion detecting sensor".

For example, in a case where the motion detecting sensor is the sensor 400 illustrated in FIG. 3, and the sensor 400 is a sensor unit equipped with the stereo camera, the processing unit 170 specifies a command corresponding to the movement by recognizing the movement of the recognition target with respect to the display screen of the display device 200. As an example of the process in the above case, the processing unit 170 specifies a distance of the recognition target with respect to the display screen of the display device 200 from the detection result output from the sensor 400, and recognizes the movement of the recognition target with respect to the display screen of the display device 200 according to a change in distance. Then, the processing unit 170 specifies the command associated to the recognized movement as the command corresponding to the motion, and performs a process corresponding to the specified command.

For example, the processing unit 170 specifies a command associated to the recognized movement by referring "a table (or a database) in which the recognized movement and the process to be performed are associated" which is stored in the storage medium such as the memory unit (not illustrated). Examples of the associating between the recognized movement and the command include "associating the recognition of a face (an example of a part of the recognition target; the same shall apply hereafter) approaching the display screen of the display device 200 and a zoom-in command" and "associating the recognition of a face approaching the display screen of the display device 200 and a zoom-out command".

Examples of the gesture recognition process include an arbitrary process capable of detecting a gesture using the motion detecting sensor such as the sensor 400 such as "a process of detecting a specific object such as a hand from the captured image and detecting a change in shape of the detected object so as to recognize a gesture" and "a process of detecting a periodic motion from the captured image so as to recognize a gesture".

For example, the processing unit 170 recognizes the gesture of the recognition target by referring information (for example, shape data as a reference for specifying a shape, periodic data as a reference for specifying a period, etc.) to recognize a gesture which is stored in the storage medium such as the memory unit (not illustrated). Then, the processing unit 170 specifies the command associated to the recognized gesture as the command corresponding to the motion, and performs a process corresponding to the specified command.

For example, the processing unit 170 specifies a command associated to the recognized gesture by referring "a table (or a database) in which the recognized gesture and the process to be performed are associated" which is stored in the storage medium such as the memory unit (not illustrated).

(d) Fourth Example of Process of Processing Unit 170

The processing unit 170 can perform two or more processes capable of being performed in parallel among the processes related to the first example described in (a) to the third example described in (c). As examples of two or more processes capable of being performed in parallel, there are "the process related to the first example described in (a) and the process related to the second example described in (b)" and "two or more processes among the process described in (c-1) to the process described in (c-3)". In a case where a plurality of processes are performed in parallel, the processing unit 170 may set priorities to the processes to be performed, and perform a process of a high priority first.

The processing unit 170 performs any one from the process related to the first example described in (a) to the process related to the fourth example described in (d) so as to perform the process corresponding to the pressing operation determined in the determination unit 168.

Further, the process performed by the processing unit 170 is not limited to the process corresponding to the pressing operation determined in the determination unit 168.

For example, in a case where the control unit 158 is configured to include no determination unit 168, the processing unit 170 performs the process associated to the pressing operation as the process corresponding to the pressing operation. The processing unit 170 performs a process which is associated to the pressing operation by being triggered at the detection of the pressing operation.

Examples of the process associated to the pressing operation performed by the processing unit 170 include a process related to the imaging operation of the imaging device 106 such as the process of changing the zoom magnification, a process related to the display of the medical captured image such as the process of changing the display mode of the screen in the display device 200, and an identification process such as the voice recognition process.

As an example, in a case where the identification process is associated to the pressing operation, the processing unit 170 transitions to a mode where the identification process based on the detection of the pressing operation is performed, and performs a process corresponding to a user's input identified in the identification process. With the execution of the process corresponding to a user's input identified in the identification process, one or both of the imaging operation of the imaging device 106 and the way of the display of the medical captured image are changed according to the user's input identified in the identification process.

In a case where the operation signal output from the operation device 300 is acquired after the process corresponding to the pressing operation is performed, the processing unit 170 stops the process being performed corresponding to the pressing operation in process based on the operation signal.

For example, in a case where the same type of the pressing operation as the type of the pressing operation corresponding to the process being performed is determined from the acquired operation signal, the processing unit 170 stops the process being performed corresponding to the pressing operation. In addition, the processing unit 170 may stop the process being performed corresponding to the pressing operation by being triggered at the acquisition (the pressing operation is detected in the detection unit 166) of the operation signal output from the operation device 300 after the process corresponding to the pressing operation is performed.

For example, the control unit 158 includes the detection unit 166, the determination unit 168, and the processing unit 170 (or one or two or more units among the imaging controller 160, the arm controller 162, and the display controller 164, and the detection unit 166, the determination unit 168, and the processing unit 170) so as to perform a leading role of the process related to the processing method according to this embodiment. In addition, the control unit 158 includes, for example, the imaging controller 160, the arm controller 162, and the display controller 164 so as to perform a role of control the entire medical observation device 100.

Further, the configuration of the control unit 158 is not limited to the example illustrated in FIG. 7.

For example, as described above, the control unit 158 may be configured not to include the determination unit 168. In a case where the determination unit 168 is not provided, the process associated to the pressing operation is performed in the control unit 158 by being triggered at the detection of the pressing operation.

In addition, the control unit 158 may be arbitrarily configured according to a method of separating the function of the medical observation device 100 such as a configuration according to a method of separating the process related to the processing method according to this embodiment.

For example, the medical observation device 100 performs the process related to the processing method according to this embodiment according to the configuration illustrated in FIG. 7.

Further, the configuration of the medical observation device according to this embodiment is not limited to the configuration illustrated in FIG. 7.

For example, the medical observation device according to this embodiment may include one or two or more units among the imaging controller 160, the arm controller 162, the display controller 164, the detection unit 166, the determination unit 168, and the processing unit 170 illustrated in FIG. 7 separately from the control unit 158 (for example, using a separate processing circuit).

In addition, the medical observation device according to this embodiment may be configured not to include the determination unit 168 for example.

In addition, the configuration to realize the process related to the processing method according to this embodiment in the medical observation device according to this embodiment is not limited to the configuration illustrated in FIG. 7. For example, the medical observation device according to this embodiment may be configured according to a method of separating the process related to the processing method according to this embodiment.

In addition, for example, when communicating with an external device through an external communication device having a function and a configuration similar to the communication unit 156, the medical observation device according to this embodiment may not include the communication unit 156.

In addition, in a case where the medical observation system according to this embodiment is configured to include the control device (not illustrated), and the medical observation device according to this embodiment is controlled by the control device (not illustrated), the medical observation device according to this embodiment may not include the control unit 158.

Herein, the control device (not illustrated) includes, for example, a control unit having a function and a configuration similar to the control unit 158. Therefore, the control device performs the process related to the processing method according to this embodiment described below, and controls the operation of components such as the arm unit 152 and the imaging unit 154 of the medical observation device according to this embodiment. The control device (not illustrated) controls the operation of the components of the medical observation device according to this embodiment by communicating with the medical observation device according to this embodiment through the equipped communication device or the connected external communication device.

Further, in a case where the medical observation system according to this embodiment is configured to include the control device (not illustrated), and the medical observation device according to this embodiment is controlled by the control device (not illustrated), the medical observation device according to this embodiment may be configured not to include some functions of the control unit 158.

[2] Processing Method According to this Embodiment

Next, the process related to the processing method according to this embodiment will be described. In the following, the description will be given about a case where the medical observation device 100 (more specifically, for example, the control unit 158 of the medical observation device 100) performs the process related to the processing method according to this embodiment. Further, as described above, the process related to the processing method according to this embodiment may be performed by the control device (not illustrated) in the medical observation system according to this embodiment.

[2-1] Outline of Processing Method According to this Embodiment

As described above, the electronic medical observation device is not configured to include an eyepiece unlike the optical medical observation device, and the imaging device can freely move. Thus, the position of an operator's face and the position of the imaging device are not constant. Therefore, even though the mouth switch is installed in the electronic medical observation device, it cannot be said that the operator can always operate the medical observation device using the mouse switch without releasing both hands in the operating field.

Thus, the medical observation device 100 has a function enabling an operation by the operation device 300 (an example of the external operation device equipped with the mouth switch; the same shall apply hereafter).

More specifically, for example, the medical observation device 100 detects the pressing operation based on the operation signal according to the pressing operation which is output from the operation device 300 (detection process). As described in the detection unit 166, the medical observation device 100 detects, for example, a specific signal pattern from the operation signal transmitted from the operation device 300 so as to detect the pressing operation on the mouth switch which includes the operation device 300.

When the pressing operation is detected, the medical observation device 100 determines a process corresponding to the pressing operation (determination process). As described in the determination unit 168, the medical observation device 100 determines, for example, a process associated to the pressing operation as the process corresponding to the pressing operation. In addition, as described in the determination unit 168, the medical observation device 100 may determine the type of the pressing operation based on the operation signal, and determine the process corresponding to the pressing operation.

Then, the medical observation device 100 performs the process corresponding to the pressing operation determined by the determination process (execution process). As described in the processing unit 170, the medical observation device 100 performs the determined process corresponding to the pressing operation by performing any one of the process related to the first example described in (a) to the process related to the fourth example described in (d).

As the process related to the processing method according to this embodiment, the detection process, the determination process, and the execution process are performed. Thus, the operator can operate the medical observation device such as changing the imaging operation of the imaging device in a surgical operation using the electronic medical observation device using the mouth switch without releasing both hands from the operating field.

Therefore, by performing the determination process and the execution process as the process related to the processing method according to this embodiment, it is possible to realize the operation of the electronic medical observation device using an external operation device equipped with the mouth switch.

Further, the process related to the processing method according to this embodiment is not limited to the detection process, the determination process, and the execution process. For example, the medical observation device 100 may not perform the determination process.

In a case where the determination process is not performed, the medical observation device 100 detects the pressing operation through the detection process, and performs the process associated to the pressing operation through the execution process by being triggered at the detection of the pressing operation.

As the process related to the processing method according to this embodiment, even in a case where the detection process, and the execution process are performed, the operator can operate the medical observation device such as changing the imaging operation of the imaging device in a surgical operation using the electronic medical observation device using the mouth switch without releasing both hands from the operating field.

Therefore, even in a case where the detection process and the execution process are performed as the process related to the processing method according to this embodiment, it is possible to realize the operation of the electronic medical observation device using an external operation device equipped with the mouth switch.

[2-2] Example of Process Related to Processing Method According to this Embodiment Next, an example of the process related to the processing method according to this embodiment will be described. In the following, the description will be given about a case where the detection process, the determination process, and the execution process are performed as the process related to the processing method according to this embodiment. Further, it is a matter of course that the example of the process related to the processing method according to this embodiment is not limited to the process related to the process related to the first example described below to the process related to the fourth example described below.

[2-2-1] First Example of Process Related to Processing Method

As the first example of the process related to the processing method, the description will be given about an example of the process of the medical observation device 100 in a case where the medical observation device 100 is operated using the operation device 300 illustrated in FIG. 4.

Figure 8:
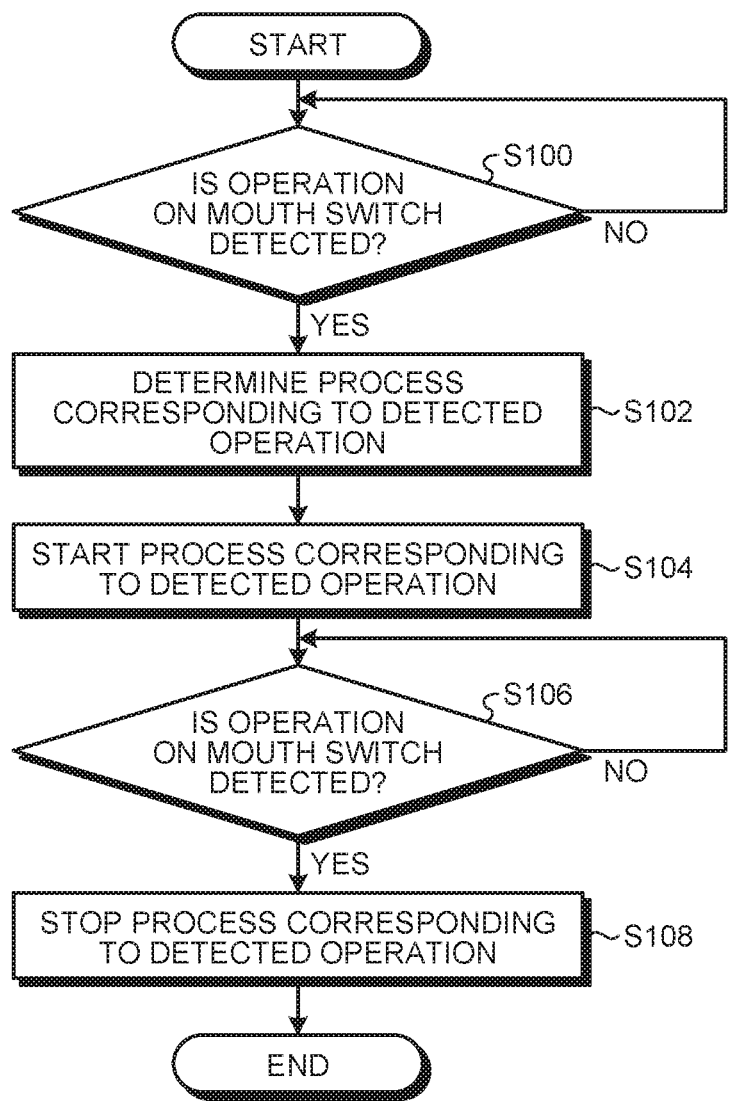
FIG. 8 is an explanatory diagram for describing a first example of a process related to a processing method according to this embodiment.

FIG. 8 is an explanatory diagram for describing the first example of the process related to the processing method according to this embodiment. For example, the process of Step S100 illustrated in FIG. 8 corresponds to the detection process related to the processing method according to this embodiment. In addition, for example, the process of Step S102 illustrated in FIG. 8 corresponds to the determination process related to the processing method according to this embodiment. The processes of Steps S104 to S108 illustrated in FIG. 8 correspond to the execution process related to the processing method according to this embodiment.

The medical observation device 100 determines whether an operation on the mouth switch is detected (S100). When the operation signal transmitted from the operation device 300 is acquired, the medical observation device 100 determines that an operation on the mouth switch is detected.

In a case where it is determined in Step S100 that an operation on the mouth switch is not detected, the medical observation device 100 does not progress the process until an operation on the mouth switch is detected.

In addition, in a case where it is determined in Step S100 that an operation on the mouth switch is detected, the medical observation device 100 determines a process corresponding to the detected operation (S102).

As described above, in a case where the medical observation device 100 controls a single function based on the operation signal acquired from the operation device 300, the medical observation device 100 determines, for example, a process associated in advance to the acquisition of the operation signal as a process corresponding to the pressing operation. As an example, in a case where it is determined that there is an operation on the mouth switch, the medical observation device 100 determines "a process of switching a display that only the medical captured image is displayed in the display screen of the display device 200 to a PIP display that the medical captured image and other images are displayed together" (an example of the process of changing the display mode of the screen).

In addition, as described above, in a case where the medical observation device 100 controls a plurality of functions based on the operation signal acquired from the operation device 300, the medical observation device 100 determines, for example, the type of the processing operation based on the operation signal. Then, the medical observation device 100 determines a process associated to the determined type of the pressing operation as a process corresponding to the pressing operation. As an example, in a case where the pressing operation is detected once within a predetermined period for determining the type of the operation, the medical observation device 100 determines the process related to zoom-in (an example of the process of changing the zoom magnification) as the process corresponding to the pressing operation. In addition, in a case where the pressing operation is detected twice within a predetermined period for determining the type of the operation, the medical observation device 100 determines the process related to zoom-out (another example of the process of changing the zoom magnification) as the process corresponding to the pressing operation.

The medical observation device 100 starts the process corresponding to the pressing operation determined in Step S102 (S104).

When the process of Step S104 is performed, the medical observation device 100 determines whether the operation on the mouth switch is detected similarly to Step S100 (S106).

In a case where it is determined in Step S106 that the operation on the mouth switch is not detected, the medical observation device 100 does not progress the process until an operation on the mouth switch is detected. In a case where it is determined in Step S106 that an operation on the mouth switch is not detected, the process corresponding to the pressing operation determined in Step S102 is kept performing.

In addition, in a case where it is determined in Step S106 that an operation on the mouth switch is detected, the medical observation device 100 stops the process corresponding to the detected operation started in Step S104 (S108).

For example, the medical observation device 100 performs the process illustrated in FIG. 8 to perform the process corresponding to the pressing operation which is performed on the operation device 300 illustrated in FIG. 4. For example, with the process illustrated in FIG. 8, the operator who uses the mouth switch of the operation device 300 can move the imaging device without releasing both hands from the operating field, and can change the imaging operation of the imaging device without releasing both hands from the operating field.

Further, it is a matter of course that the process of the medical observation device 100 in a case where the medical observation device 100 is operated using the operation device 300 illustrated in FIG. 4 is not limited to the example illustrated in FIG. 8.

[2-2-2] Second Example of Process Related to Processing Method

As the second example of the process related to the processing method, the description will be given about an example of the process of the medical observation device 100 in a case where the medical observation device 100 is operated using the operation device 300 illustrated in FIG. 5.

Figure 9:
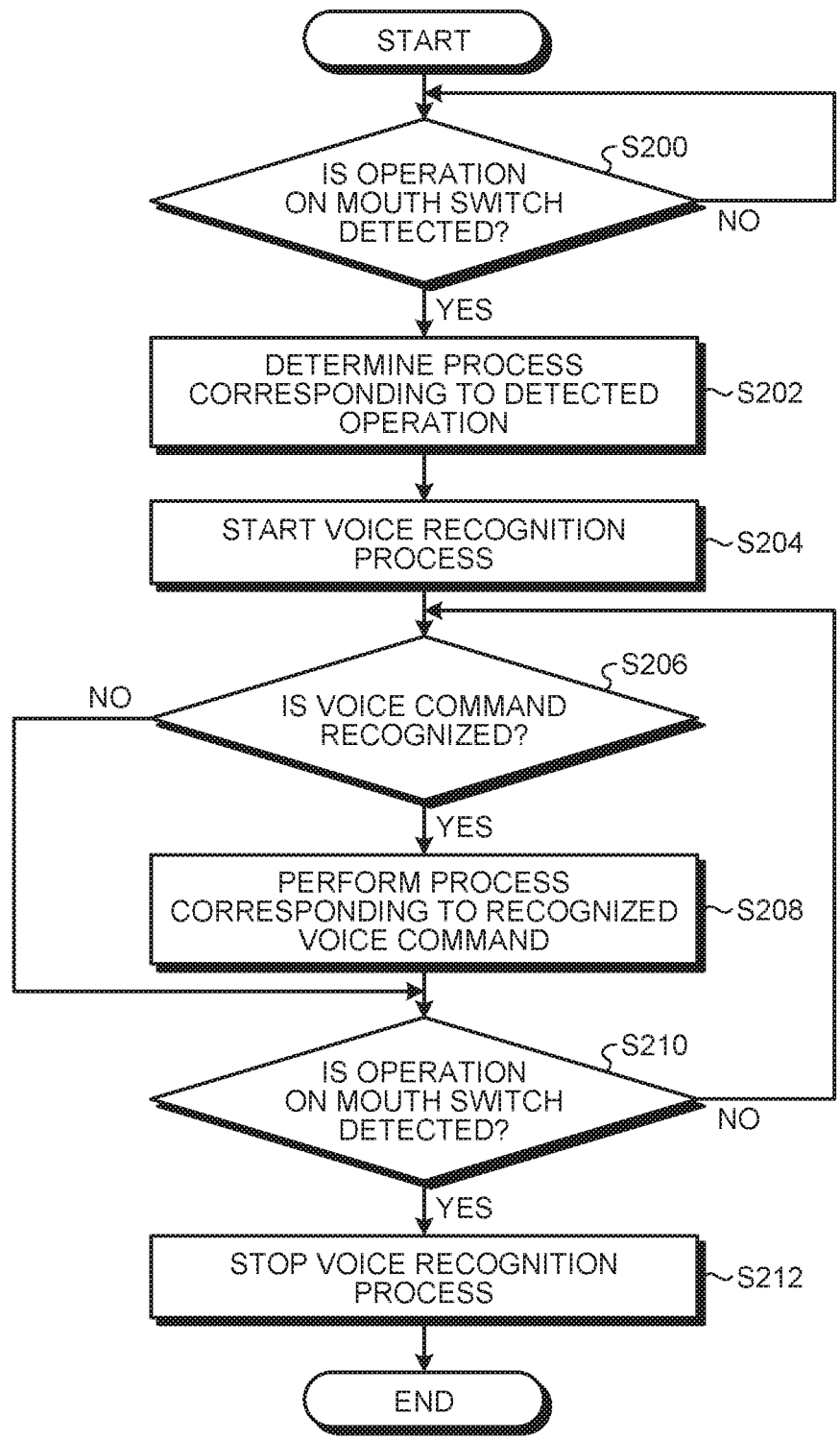
FIG. 9 is an explanatory diagram for describing a second example of a process related to the processing method according to this embodiment.

FIG. 9 is an explanatory diagram for describing the second example of the process related to the processing method according to this embodiment. For example, the process of Step S200 illustrated in FIG. 9 corresponds to the detection process related to the processing method according to this embodiment. In addition, for example, the process of Step S202 illustrated in FIG. 9 corresponds to the determination process related to the processing method according to this embodiment. The processes of Steps S204 to S212 illustrated in FIG. 9 correspond to the execution process related to the processing method according to this embodiment.

The medical observation device 100 determines whether the operation on the mouth switch is detected similarly to Step S100 of FIG. 8 (S200).

In a case where it is determined in Step S200 that the operation on the mouth switch is not detected, the medical observation device 100 does not progress the process until an operation on the mouth switch is detected.

In addition, in a case where it is determined in Step S200 that an operation on the mouth switch is detected, the medical observation device 100 determines a process corresponding to the detected operation similarly to Step S102 of FIG. 8 (S202). In the following, the description will be given about a case where the voice recognition process (an example of the identification process) is determined in Step S202 as a process corresponding to the detected operation.

The medical observation device 100 starts the voice recognition process which is determined in Step S202 (S204).

The medical observation device 100 determines whether the voice command is recognized from the voice signal output from the voice input device 304 of the operation device 300 (S206). For example, in a case where the medical observation device 100 is assigned with a name, the voice command recognizable to the medical observation device 100 may be "the name of the medical observation device 100 and the command". In a case where the voice command recognizable to the medical observation device 100 is "the name of the medical observation device 100 and the command", it is possible to improve convenience for the operator of the operation device 300 compared to a case where the voice command is simply the "command".

In a case where it is determined in Step S206 that the voice command is not recognized, the medical observation device 100 performs the process of Step S210 described below.

In a case where it is determined in Step S206 that the voice command is recognized, the medical observation device 100 performs a process corresponding to the recognized voice command (S208). Examples of the process corresponding to the voice command include "a process related to the imaging operation of the imaging device 106 such as zoom-in, zoom-out, focus-in, and focus-out", "a process related to the operation of the arm 104 to move the imaging device 106 right and left, up and down", and "a process of switching a display that only the medical captured image is displayed in the display screen of the display device 200 to a PIP display that the medical captured image and other images are displayed together".

In a case where the process of Step S208 is performed, or it is determined in Step S206 that the voice command is not recognized, the medical observation device 100 determines whether an operation on the mouth switch is detected similarly to Step S100 of FIG. 8 (S210).

In a case where it is determined in Step S210 that an operation on the mouth switch is not detected, the medical observation device 100 repeatedly performs the processes from Step S206.

In addition, in a case where it is determined in Step S210 that an operation on the mouth switch is detected, the medical observation device 100 stops the voice recognition process started in Step S204 (S212).

For example, the medical observation device 100 performs the process illustrated in FIG. 9 to perform the process corresponding to the pressing operation which is performed on the operation device 300 illustrated in FIG. 5. For example, a voice UI is started and stopped by being triggered at the pressing operation on the mouth switch with the process illustrated in FIG. 9. Therefore, the operator can operate various functions of the medical observation device 100 by voice by turning on/off the voice UI without releasing both hands from the operating field.

Further, the process of the medical observation device 100 in a case where the medical observation device 100 is operated using the operation device 300 illustrated in FIG. 5 is not limited to the example illustrated in FIG. 9. For example, the description in FIG. 9 has been given about an example that the voice recognition process is determined in Step S202, and the voice recognition process is performed. The processes other than the voice recognition process may be performed. In a case where the processes other than the voice recognition process is performed as a process corresponding to the detected operation, the medical observation device 100 performs the processes similar to those after Step S104 of FIG. 8 as the processes after Step S204 of FIG. 9 for example.

[2-2-3] Third Example of Process Related to Processing Method

As the third example of the process related to the processing method, the description will be given about an example of the process of the medical observation device 100 in the medical observation system equipped with the sensor 400 illustrated in FIG. 3.

In the following, it will be exemplified a case where the sensor 400 is "a sensor unit which includes a stereo camera and a processor, and detects at least the line of vision from the captured image which is captured by the stereo camera" (that is, the sensor 400 has the function as a line-of-vision detecting sensor). In the medical observation system equipped with the sensor 400, the medical observation device 100 is operated using the operation device 300 illustrated in FIG. 4 or the operation device 300 illustrated in FIG. 5.

Figure 10:
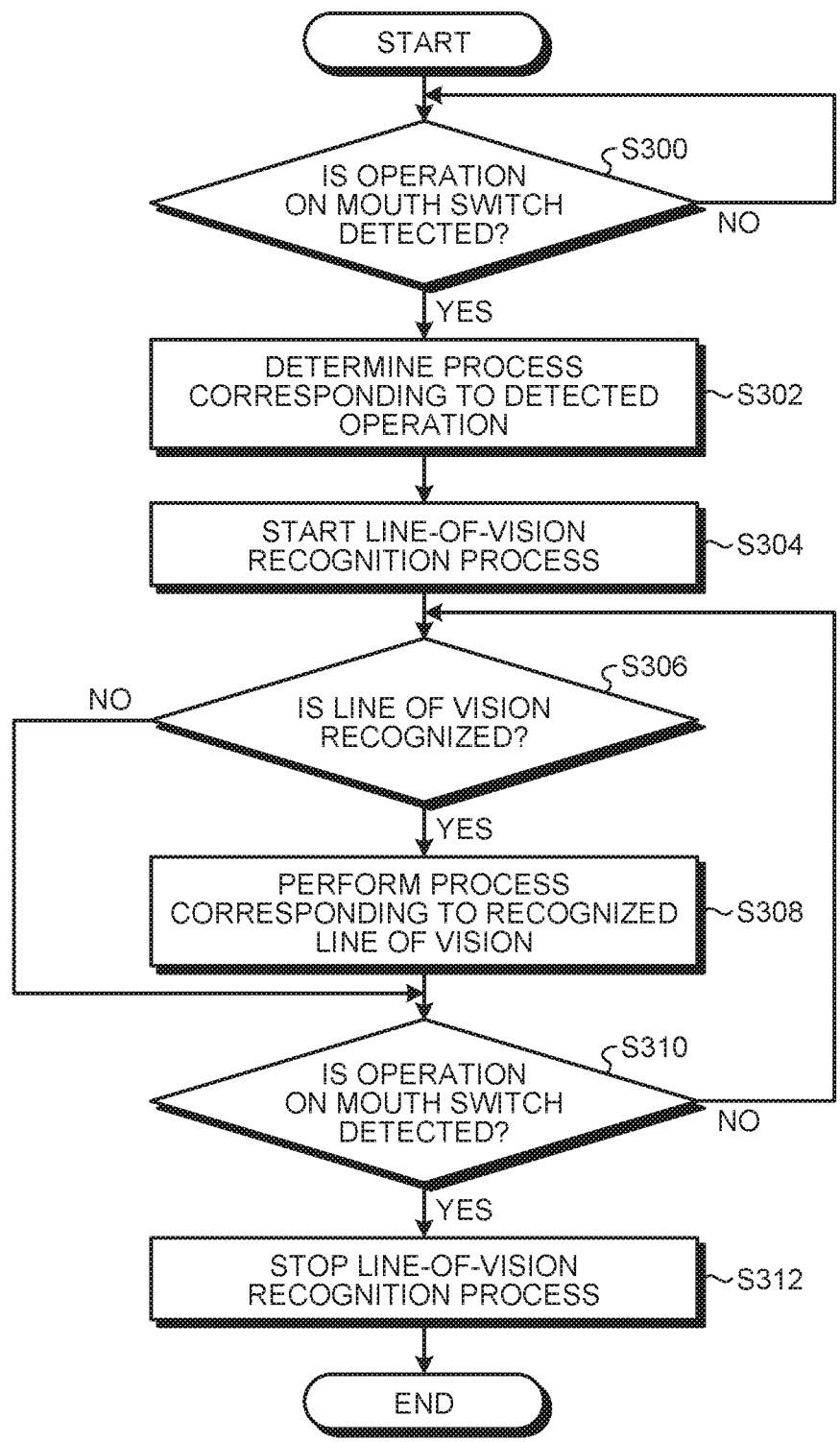
FIG. 10 is an explanatory diagram for describing a third example of a process related to the processing method according to this embodiment.

FIG. 10 is an explanatory diagram for describing the third example of the process related to the processing method according to this embodiment. For example, the process of Step S300 illustrated in FIG. 10 corresponds to the detection process related to the processing method according to this embodiment. In addition, for example, the process of Step S302 illustrated in FIG. 10 corresponds to the determination process related to the processing method according to this embodiment. The processes of Steps S304 to S312 illustrated in FIG. 10 correspond to the execution process related to the processing method according to this embodiment.

The medical observation device 100 determines whether the operation on the mouth switch is detected similarly to Step S100 of FIG. 8 (S300).

In a case where it is determined in Step S300 that the operation on the mouth switch is not detected, the medical observation device 100 does not progress the process until an operation on the mouth switch is detected.

In addition, in a case where it is determined in Step S300 that an operation on the mouth switch is detected, the medical observation device 100 determines a process corresponding to the detected operation similarly to Step S102 of FIG. 8 (S302). In the following, the description will be given about a case where the line-of-vision recognition process (an example of the identification process) is determined in Step S302 as a process corresponding to the detected operation.

The medical observation device 100 starts the line-of-vision recognition process which is determined in Step S302 (S304).

The medical observation device 100 determines whether the line of vision is recognized based on the detection result output from the sensor 400 which serves as the line-of-vision detecting sensor (S306).

In a case where it is determined in Step S306 that the line of vision is not recognized, the medical observation device 100 performs the process of Step S310 described below.

In a case where it is determined in Step S306 that the line of vision is recognized, the medical observation device 100 performs a process corresponding to the recognized line of vision (S308). As a process corresponding to the recognized line of vision, for example, there is a process of using the recognized line of vision such as "a process in which, when the line of vision moves on the display screen of the display device 200 displayed by the medical captured image, the arm 104 is controlled to display the portion of the medical captured image corresponding to the position of the line of vision at the center position of the display screen so as to move the imaging device 106".

In a case where the process of Step S308 is performed, or it is determined in Step S206 that the line of vision is not recognized, the medical observation device 100 determines whether an operation on the mouth switch is detected similarly to Step S100 of FIG. 8 (S310).

In a case where it is determined in Step S310 that an operation on the mouth switch is not detected, the medical observation device 100 repeatedly performs the processes from Step S306.

In addition, in a case where it is determined in Step S310 that an operation on the mouth switch is detected, the medical observation device 100 stops the line-of-vision recognition process started in Step S304 (S312).

For example, the medical observation device 100 performs the process illustrated in FIG. 10 to perform the process corresponding to the pressing operation which is performed on the operation device 300 in the medical observation system equipped with the sensor 400. For example, a line-of-vision UI is started and stopped by being triggered at the pressing operation on the mouth switch with the process illustrated in FIG. 10. Therefore, the operator who uses the operation device 300 can move the imaging device 106 only by the line of vision without using both hands.

Further, the process of the medical observation device 100 in the medical observation system equipped with the sensor 400 is not limited to the example illustrated in FIG. 10. For example, the description in FIG. 10 has been given about an example that the line-of-vision recognition process is determined in Step S302, and the line-of-vision recognition process is performed. The processes other than the line-of-vision recognition process may be performed. In a case where the processes other than the line-of-vision recognition process is performed as a process corresponding to the detected operation, the medical observation device 100 performs the processes similar to those after Step S104 of FIG. 8 as the processes after Step S304 of FIG. 10 for example. In addition, in a case where the processes other than the line-of-vision recognition process is performed as a process corresponding to the detected operation, the medical observation device 100 may perform the processes similar to those after Step S204 of FIG. 9 as the processes after Step S304 of FIG. 10 for example. In addition, in the medical observation system equipped with the sensor 400, the medical observation device 100 can also perform the process related to the fourth example described below.

[2-2-4] Fourth Example of Process Related to Processing Method

As the fourth example of the process related to the processing method, the description will be given about another example of the process of the medical observation device 100 in the medical observation system equipped with the sensor 400 illustrated in FIG. 3.

In the following, it will be exemplified a case where the sensor 400 is "a sensor unit which includes a stereo camera and a processor, and detects at least the motion from the captured image which is captured by the stereo camera" (that is, the sensor 400 has the function as a motion detecting sensor). In the medical observation system equipped with the sensor 400, the medical observation device 100 is operated using the operation device 300 illustrated in FIG. 4 or the operation device 300 illustrated in FIG. 5.

Figure 11:
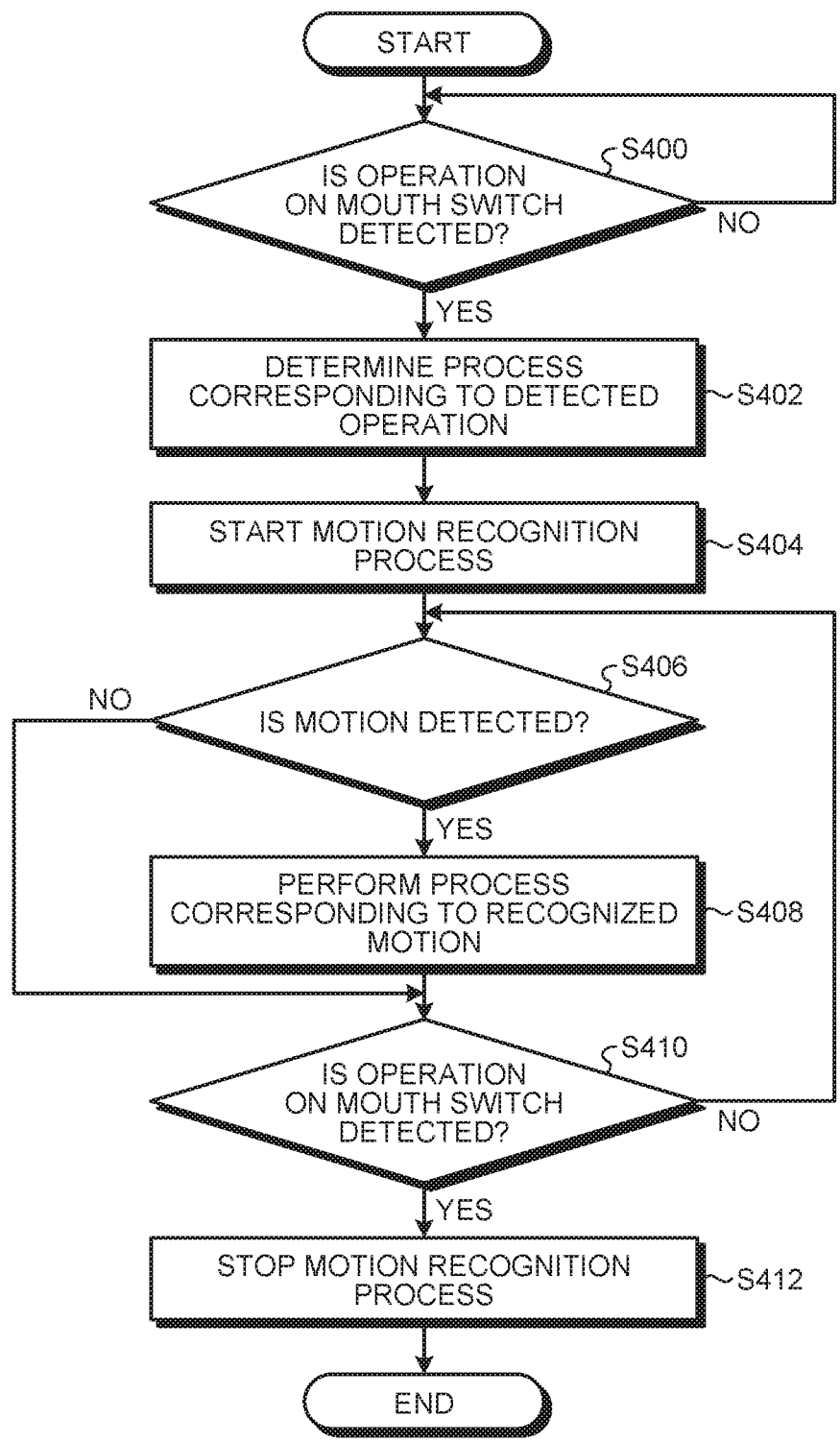
FIG. 11 is an explanatory diagram for describing a fourth example of a process related to the processing method according to this embodiment.

FIG. 11 is an explanatory diagram for describing the fourth example of the process related to the processing method according to this embodiment. For example, the process of Step S400 illustrated in FIG. 11 corresponds to the detection process related to the processing method according to this embodiment. In addition, for example, the process of Step S402 illustrated in FIG. 11 corresponds to the determination process related to the processing method according to this embodiment. The processes of Steps S404 to S412 illustrated in FIG. 11 correspond to the execution process related to the processing method according to this embodiment.

The medical observation device 100 determines whether the operation on the mouth switch is detected similarly to Step S100 of FIG. 8 (S400).

In a case where it is determined in Step S400 that the operation on the mouth switch is not detected, the medical observation device 100 does not progress the process until an operation on the mouth switch is detected.

In addition, in a case where it is determined in Step S400 that an operation on the mouth switch is detected, the medical observation device 100 determines a process corresponding to the detected operation similarly to Step S102 of FIG. 8 (S402). In the following, the description will be given about a case where the motion recognition process (an example of the identification process) is determined in Step S402 as a process corresponding to the detected operation.

The medical observation device 100 starts the motion recognition process which is determined in Step S402 (S404).

The medical observation device 100 determines whether the motion is recognized based on the detection result output from the sensor 400 which serves as the motion detecting sensor (S406).

In a case where it is determined in Step S406 that the motion is not recognized, the medical observation device 100 performs the process of Step S410 described below.

In a case where it is determined in Step S406 that the motion is recognized, the medical observation device 100 performs a process corresponding to the recognized motion (S408). Examples of processes corresponding to the recognized motion include "a process of zooming in the imaging device 106 when a face is recognized to come close to the display screen of the display device 200", and "a process of zooming out the imaging device 106 when a face is recognized to go away from the display screen of the display device 200". In addition, the process corresponding to the recognized motion may be a process of associating a recognized gesture.

In a case where the process of Step S408 is performed, or it is determined in Step S406 that the motion is not recognized, the medical observation device 100 determines whether an operation on the mouth switch is detected similarly to Step S100 of FIG. 8 (S410).

In a case where it is determined in Step S410 that an operation on the mouth switch is not detected, the medical observation device 100 repeatedly performs the processes from Step S406.

In addition, in a case where it is determined in Step S410 that an operation on the mouth switch is detected, the medical observation device 100 stops the motion recognition process started in Step S404 (S412).

For example, the medical observation device 100 performs the process illustrated in FIG. 11 to perform the process corresponding to the pressing operation which is performed on the operation device 300 in the medical observation system equipped with the sensor 400. For example, a motion UI is started and stopped by being triggered at the pressing operation on the mouth switch with the process illustrated in FIG. 11. Therefore, the operator who uses the operation device 300 can control an imaging function of the imaging device 106 such as the zoom function of the imaging device 106 only by a motion of the face without using both hands.

Further, the process of the medical observation device 100 in the medical observation system equipped with the sensor 400 is not limited to the example illustrated in FIG. 11. For example, the description in FIG. 11 has been given about an example that the motion recognition process is determined in Step S402, and the motion recognition process is performed. The processes other than the motion recognition process may be performed. In a case where the processes other than the motion recognition process is performed as a process corresponding to the detected operation, the medical observation device 100 performs the processes similar to those after Step S104 of FIG. 8 as the processes after Step S404 of FIG. 11 for example. In addition, in a case where the processes other than the motion recognition process is performed as a process corresponding to the detected operation, the medical observation device 100 may perform the processes similar to those after Step S204 of FIG. 9 as the processes after Step S404 of FIG. 11 for example.

[3] Example of Effect Obtained by Using Medical Information Processing System According to this Embodiment With the use of the medical information processing system according to this embodiment, the following effects are achieved for example. Further, it is a matter of course that the effects achieved by using the medical information processing system according to this embodiment are not limited to the following example.

In a surgical operation using the electronic medical observation device, the operator who uses the mouth switch of the operation device 300 can move the imaging device without releasing both hands from the operating field, and can change the imaging operation of the imaging device without releasing both hands from the operating field.

The voice UI is started and stopped by being triggered at the pressing operation on the mouth switch. Therefore, the operator can operate various functions of the medical observation device 100 by voice by turning on/off the voice UI without releasing both hands from the operating field.

The line-of-vision UI is started and stopped by being triggered at the pressing operation on the mouth switch. Therefore, the operator can move the imaging device 106 only by the line of vision without using both hands.

The motion UI is started and stopped by being triggered at the pressing operation on the mouth switch. Therefore, the operator can control an imaging function of the imaging device 106 such as the zoom function of the imaging device 106 only by a motion of the face without using both hands.

Program According to this Embodiment

A program (for example, a program capable of performing the process related to the processing method according to this embodiment such as "the detection process and the execution process" according to this embodiment, and "the detection process, the determination process, and the execution process") which causes a computer system to serve as the medical observation device according to this embodiment (or a control device), when executed by a processor in the computer system, can operate the medical observation device by an external operation device equipped with a switch which is pressed by a mouth. Herein, a single computer or a plurality of computers may be used as the computer system according to this embodiment. As the computer system according to this embodiment, a series of processes of the processing method according to this embodiment is performed.

In addition, the program causing the computer system to serve as the medical observation device according to this embodiment (or the control device according to this embodiment) is performed by the processor in the computer system, so that the effects obtained by the display realized by the process related to the processing method according to this embodiment can be achieved.

Hitherto, the preferred embodiments of the present disclosure have been described in detail with reference to the accompanying drawings. However, the technical scope of the present disclosure is not limited to the examples. It is a matter of course that a person having ordinary skills in the technical field of the present disclosure can conceive various changes and modifications within a scope of the technical ideas disclosed in claims, which are considered to belong to the technical scope of the present disclosure.

For example, in the above description, the program (computer program) to cause the computer system to serve as the medical observation device according to this embodiment is provided. However, this embodiment can also provide a storage medium to store the program.

The above configuration is given as an example of this embodiment, and of course belongs to the technical scope of the present disclosure.

In addition, the effects described in the specification are given as merely explanatory or exemplary, but not limited. In other words, the technique according to the present disclosure can achieve the above effects, or can other effects that are clear to a person skilled in the art from the description of the specification instead of the above effects.

Further, the following configurations also belong to the technical scope of the present disclosure.

(1)

A medical observation device, including:

a detection unit configured to detect a pressing operation based on an operation signal according to the pressing operation which is output from an external operation device equipped with a switch pressed by a mouth; and a processing unit which performs a process corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

(2)

The medical observation device according to (1), wherein the processing unit is configured to transition to a mode for performing the identification process based on the detection of the pressing operation, and perform a process corresponding to a user's input which is identified by the identification process.

(3)

The medical observation device according to (2), wherein the processing unit is configured to perform a voice recognition process, as the identification process, on a voice signal which is output from the voice input device, and perform a process corresponding to the recognized voice input.

(4)

The medical observation device according to (3), wherein the voice input device is a voice input device which is provided in the external operation device.

(5)

The medical observation device according to any one of (2) to (4), wherein the processing unit is configured to perform a line-of-vision recognition process, as the identification process, in which a line of vision of a recognition target is recognized, and perform a process corresponding to the recognized line-of-vision input.

(6)

The medical observation device according to any one of (2) to (4), wherein the processing unit is configured to perform a motion recognition process, as the identification process, in which a motion of a recognition target is recognized, and perform a process corresponding to the recognized motion input.

(7)

The medical observation device according to (6), wherein the motion recognition process is a movement recognition process in which a movement of the recognition target is recognized.

(8)

The medical observation device according to (6) or (7), wherein the motion recognition process is a gesture recognition process in which a gesture of the recognition target is recognized.

(9)

The medical observation device according to any one of (5) to (8), wherein the processing unit sets an operator who uses the external operation device as the recognition target.

(10)

The medical observation device according to any one of (1) to (9), wherein the processing unit performs a process associated to the pressing operation as the process corresponding to the pressing operation.

(11)

The medical observation device according to any one of (1) to (9), further including:

a determination unit which determines the process corresponding to the detected pressing operation based on the operation signal, wherein the processing unit performs the determined process corresponding to the pressing operation.

(12)

The medical observation device according to (11), wherein the determination unit is configured to determine a type of the pressing operation based on the operation signal, and determine a process associated to the determined type of the pressing operation as the process corresponding to the pressing operation.

(13)

The medical observation device according to any one of (1) to (12), wherein the process related to the imaging operation of the imaging device includes one or two or more processes of changing a zoom magnification, adjusting a focus position, changing an imaging position, changing a focal depth, and changing an observation mode.

(14)

The medical observation device according to any one of (1) to (13), wherein the process related to a display of the medical captured image includes one or both of changing a display mode of a screen and changing a color mode.

(15)

The medical observation device according to any one of (1) to (14), wherein the processing unit stops the process being performed corresponding to the pressing operation based on the operation signal output from the external operation device.

(16)

The medical observation device according to any one of (1) to (15), including:

an arm which is configured by a plurality of links connected to each other by joint portions; and the imaging device which is supported by the arm.

(17)

A processing method which is performed by a medical observation device including:

detecting a pressing operation based on an operation signal according to the pressing operation which is output from an external operation device equipped with a switch pressed by a mouth; and performing a process corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

(18) A medical observation system, including:
an operation device which includes a switch which is pressed by a mouth; and
a medical observation device,
wherein the medical observation device includes
an imaging device,
a detection unit which detects the pressing operation based on an operation signal according to the pressing operation output from the operation device, and
a processing unit which performs a process corresponding to the detected pressing operation, and
wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image.

REFERENCE SIGNS LIST

100 MEDICAL OBSERVATION DEVICE
102 BASE
104 ARM
106 IMAGING DEVICE
110a, 110b, 110c, 110d, 110e, 110f JOINT PORTION
112a, 112b, 112c, 112d, 112e, 112f LINK
120 IMAGING MEMBER
122 CYLINDRICAL MEMBER
124 ZOOM SWITCH
126 FOCUS SWITCH
128 OPERATION MODE CHANGE SWITCH
152 ARM UNIT
154 IMAGING UNIT
156 COMMUNICATION UNIT
158 CONTROL UNIT
160 IMAGING CONTROLLER
162 ARM CONTROLLER
164 DISPLAY CONTROLLER
166 DETECTION UNIT
168 DETERMINATION UNIT
170 PROCESSING UNIT
200 DISPLAY DEVICE
300 OPERATION DEVICE
400 SENSOR
1000 MEDICAL OBSERVATION SYSTEM
OP OPERATOR
PA PATIENT
FS FOOT SWITCH

The invention claimed is:

1. A medical observation device, comprising:
processing circuitry configured to
detect a pressing operation based on an operation signal according to the pressing operation output from an external operation device equipped with a switch pressed by a mouth; and
perform a process of controlling the medical observation device corresponding to the detected pressing operation, wherein
the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image,
the processing circuitry is further configured to
switch to a mode for performing the identification process based on the detection of the pressing operation,
perform a process corresponding to the user's input identified by the identification process,
perform a voice recognition process of recognizing voice, as the identification process, on a voice signal output from a voice input device, and
perform a process corresponding to the recognized voice.

2. The medical observation device according to claim 1, wherein the voice input device is provided in the external operation device.

3. The medical observation device according to claim 1, wherein the processing circuitry is configured to perform a process associated to the pressing operation as the process corresponding to the pressing operation.

4. The medical observation device according to claim 1, wherein the processing circuitry is configured to:
determine the process corresponding to the detected pressing operation based on the operation signal, and
perform the determined process corresponding to the pressing operation.

5. The medical observation device according to claim 4, wherein the processing circuitry is configured to:
determine a type of the pressing operation based on the operation signal, and
determine a process associated to the determined type of the pressing operation as the process corresponding to the pressing operation.

6. The medical observation device according to claim 1, wherein the process related to the imaging operation of the imaging device includes one or two or more processes of changing a zoom magnification, adjusting a focus position, changing an imaging position, changing a focal depth, and changing an observation mode.

7. The medical observation device according to claim 1, wherein the process related to a display of the medical captured image includes one or both of changing a display mode of a screen and changing a color mode.

8. The medical observation device according to claim 1, wherein the processing circuitry is configured to stop the process being performed corresponding to the pressing operation based on the operation signal output from the external operation device.

9. The medical observation device according to claim 1, comprising:
an arm configured by a plurality of links connected to each other by joint portions; and
the imaging device supported by the arm.

10. The medical observation device according to claim 1, further comprising:
the external operation device including the switch.

11. A medical observation device, comprising:
processing circuitry configured to
detect a pressing operation based on an operation signal according to the pressing operation output from an external operation device equipped with a switch pressed by a mouth; and perform a process of controlling the medical observation device corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image, the processing circuitry is further configured to
switch to a mode for performing the identification process based on the detection of the pressing operation,
perform a process corresponding to the user's input identified by the identification process,
perform a line-of-vision recognition process, as the identification process, in which a line of vision of a recognition target is recognized, and
perform a process corresponding to the recognized line-of-vision.

12. The medical observation device according to claim 11, wherein the processing circuitry is configured to set an operator who uses the external operation device as the recognition target.

13. The medical observation device according to claim 11, further comprising:
the external operation device including the switch.

14. The medical observation device according to claim 11, comprising:
an arm configured by a plurality of links connected to each other by joint portions; and
the imaging device supported by the arm.

15. A medical observation device, comprising:
processing circuitry configured to
detect a pressing operation based on an operation signal according to the pressing operation output from an external operation device equipped with a switch pressed by a mouth; and
perform a process of controlling the medical observation device corresponding to the detected pressing operation, wherein the process corresponding to the pressing operation includes some or all of a process related to an imaging operation of an imaging device, a process related to a display of a medical captured image which is captured in the imaging device, and an identification process of identifying a user's input indicating the process related to the imaging operation or the process related to the display of the medical captured image, the processing circuitry is further configured to
switch to a mode for performing the identification process based on the detection of the pressing operation,
perform a process corresponding to the user's input identified by the identification process;
perform a motion recognition process, as the identification process, in which a motion of a recognition target is recognized, and
perform a process corresponding to the recognized motion.

16. The medical observation device according to claim 15, wherein a movement of the recognition target is recognized in the motion recognition process.

17. The medical observation device according to claim 15, wherein the motion recognition process is a gesture recognition process in which a gesture of the recognition target is recognized.

18. The medical observation device according to claim 15, further comprising:
the external operation device including the switch.

19. The medical observation device according to claim 15, comprising:
an arm configured by a plurality of links connected to each other by joint portions; and
the imaging device supported by the arm.

* * * * *